(12) United States Patent
Salamatian et al.

(10) Patent No.: US 10,575,759 B2
(45) Date of Patent: Mar. 3, 2020

(54) METHOD AND SYSTEM FOR MONITORING AND ANALYZING POSITION, MOTION, AND EQUILIBRIUM OF BODY PARTS

(71) Applicant: BaziFIT, Inc., Boulder, CO (US)

(72) Inventors: Tallis Anthony Salamatian, Boulder, CO (US); Chris Lehman, San Francisco, CA (US); Douglas Ross, Sacramento, CA (US); Gregory Bland, Boulder, CO (US); Emil Valchinov, Patra (GR)

(73) Assignee: BaziFIT, Inc., Boulder, CO (US)

(*) Notice: Subject to any disclaimer, the term of this patent is extended or adjusted under 35 U.S.C. 154(b) by 10 days.

(21) Appl. No.: 15/201,359

(22) Filed: Jul. 1, 2016

(65) Prior Publication Data
US 2017/0000386 A1 Jan. 5, 2017

Related U.S. Application Data

(60) Provisional application No. 62/187,725, filed on Jul. 1, 2015.

(51) Int. Cl.
*A63B 24/00* (2006.01)
*A61B 5/11* (2006.01)
(Continued)

(52) U.S. Cl.
CPC ........... *A61B 5/1114* (2013.01); *A61B 5/1122* (2013.01); *A61B 5/6802* (2013.01); (Continued)

(58) Field of Classification Search
CPC ............ A63B 21/0724; A63B 21/0552; A63B 26/003; A63B 2220/40; A63B 2220/10; (Continued)

(56) References Cited

U.S. PATENT DOCUMENTS 7,602,301 B1 * 10/2009 Stirling ................ A61B 5/1127
340/573.1
2018/0001184 A1 * 1/2018 Tran ..................... H04N 5/2257
(Continued)

*Primary Examiner* — Glenn Richman
(74) *Attorney, Agent, or Firm* — Madan Law PLLC

(57) ABSTRACT

Systems, methods, and computer program products which facilitate the ability of a user to monitor and assess the location of and forces transferred to various joints, muscles, and limbs and their relative positions at each and every moment during normal daily activities, training loads of an exercise, or a competitive or high intensity athletic endeavors, in order to mitigate and reduce the risk of injury as well as to track fitness performance elements are disclosed. In an aspect, systems, methods, and computer program products are disclosed which utilize at least one sensor in order to capture a user's movement information during various tasks and exercises. This movement information may then be analyzed in order to determine quantifiable values for the user's likelihood of experiencing an injury and/or the user's overall fitness, generally. The systems, methods, and computer program products of the present disclosure may also be used to measure a user's neuromuscular efficiency and help the user make improvements thereto.

6 Claims, 29 Drawing Sheets

(51) Int. Cl.

| | | |
|---|---|---|
| *G06F 19/00* | (2018.01) | |
| *A61B 5/00* | (2006.01) | |
| *A63C 5/06* | (2006.01) | |
| *A63C 17/00* | (2006.01) | |
| *A63F 13/00* | (2014.01) | |
| *G01S 19/19* | (2010.01) | |
| *G06Q 50/00* | (2012.01) | |
| *H04L 29/06* | (2006.01) | |
| *A63F 13/211* | (2014.01) | |
| *A63F 13/537* | (2014.01) | |
| *A63F 13/92* | (2014.01) | |
| *A63F 13/214* | (2014.01) | |
| *A63B 21/072* | (2006.01) | |
| *A63B 26/00* | (2006.01) | |
| *A63B 21/055* | (2006.01) | |
| *A63B 22/18* | (2006.01) | |
| *A63B 23/04* | (2006.01) | |
| *A63B 71/06* | (2006.01) | |

(52) U.S. Cl.
CPC ............ *A61B 5/7275* (2013.01); *A61B 5/742* (2013.01); *A63C 5/06* (2013.01); *A63C 17/0006* (2013.01); *A63F 13/00* (2013.01); *A63F 13/211* (2014.09); *A63F 13/214* (2014.09); *A63F 13/537* (2014.09); *A63F 13/92* (2014.09); *G01S 19/19* (2013.01); *G06F 19/3481* (2013.01); *G06Q 50/01* (2013.01); *H04L 29/06* (2013.01); *A63B 21/0552* (2013.01); *A63B 21/0724* (2013.01); *A63B 22/18* (2013.01); *A63B 26/003* (2013.01); *A63B 2023/0411* (2013.01); *A63B 2071/065* (2013.01); *A63B 2071/068* (2013.01); *A63B 2071/0625* (2013.01); *A63B 2071/0683* (2013.01); *A63B 2207/02* (2013.01); *A63B 2220/10* (2013.01); *A63B 2220/12* (2013.01); *A63B 2220/36* (2013.01); *A63B 2220/40* (2013.01); *A63B 2220/803* (2013.01); *A63B 2220/806* (2013.01); *A63B 2225/15* (2013.01); *A63B 2225/20* (2013.01); *A63B 2225/50* (2013.01); *A63B 2225/54* (2013.01); *A63B 2230/06* (2013.01); *A63B 2230/42* (2013.01); *A63B 2230/60* (2013.01); *A63B 2230/75* (2013.01)

(58) Field of Classification Search
CPC ............ A63B 2220/12; A63B 2220/36; A63B 2220/803; A63B 2220/806; A63B 2225/15; A63B 2225/20; A63B 2225/50; A63B 2071/0625; A63B 2071/065; A63B 2071/068; A63B 2071/0683; A63B 2207/02; A61B 5/1114; A61B 5/1122; A61B 5/6802; A61B 5/742; A61B 5/7275
See application file for complete search history.

(56) References Cited

U.S. PATENT DOCUMENTS

| | | | |
|---|---|---|---|
| 2018/0021653 A1* | 1/2018 | Thornbrue | G06F 19/00 473/453 |
| 2018/0160943 A1* | 6/2018 | Fyfe | A63B 71/06 |
| 2018/0161623 A1* | 6/2018 | Nejezchleb | A63B 24/0006 |
| 2018/0168518 A1* | 6/2018 | Kaleal, III | A61B 5/4872 |

* cited by examiner

METHOD AND SYSTEM FOR MONITORING AND ANALYZING POSITION, MOTION, AND EQUILIBRIUM OF BODY PARTS

FIELD OF THE DISCLOSURE

The present disclosure relates generally to a system and method for monitoring and analyzing a moving body's position, motion, and equilibrium. More particularly, the present disclosure relates to a system and method, which assesses an individual's injury risk, healing stage, fitness level, and overall performance for a particular part of body based on its position, motion, and equipoise.

BACKGROUND OF THE DISCLOSURE

In recent years, there has been an increasing interest in the use of technology to assess forces transferred to various joints, muscles, and limbs and their relative positions to each other as well as their global position at each and every moment during normal daily activities, during training loads of an exercise, or during a competitive or high intensity athletic endeavor. Efforts have been made to utilize global positioning system (GPS) devices to record running speed and estimate running performance, or to monitor human body movement and create a movement economy profile using data from measurement devices determining general body movement relative to the speed of the human body, or to estimate muscle power and joint force of limbs in order to obtain skill-related fitness parameters corresponding to the sensing of a sensing module. These known prior arts are as follows:

- US 20140300490 A1, Wearable computing device for secure control of physiological sensors and medical devices, with secure storage of medical records, and bioimpedance biometric
- US 20110246123 A1, Personal Status Monitoring
- WO2009042390//US20120130673//U.S. Pat. No. 8,461,999 B2, Capturing body movement related to a fixed coordinate system
- WO 2013063159 A2//US20130150121, Method to provide dynamic customized sports instruction responsive to motion of a mobile device
- US 20120046901 A1, Motion capture apparatus
- WO 2014043757 A1, Stride detection
- US 20110092860 A1, System for clinical assessment of movement disorders
- U.S. Pat. No. 8,821,417 B2, Method of monitoring human body movement
- WO 2013072234 A1, Physical exercise correctness calculation method and system
- U.S. Pat. No. 8,523,741 B2, Method and system for monitoring sport related fitness by estimating muscle power and joint force of limbs
- WO 2010055352 A1//US20110218463, Assessment of gait
- WO 2005002436 A1, Motion monitoring and analysis system
- WO 2002018019 A1, Rehabilitation device In general, rate of anterior cruciate ligament (ACL) injuries per student athlete and among young people in high school and college is very high. For instance, one in every hundred college basketball players tears his or her ACL every year. So, just in Washington, D.C. metro area, in terms of the college basketball teams at George Mason, Georgetown and GW, roughly one basketball player tears their ACL every year. High school athletes also bear an extremely high risk of getting hurt. The incidence of ACL injuries is currently estimated at approximately 200,000 annually, with 100,000 ACL reconstructions performed each year.

Over 70% of ACL tears occur in a non-contact mechanism; that is, an injury happening during one body's own activity with no contact or direct involvement of others—no tackle hit, or even a touch from others. A tear occurs in a non-contact mechanism when forces generated by the body during an activity are not controlled properly, allowing excess forces to be transferred to the ACL, resulting in a tear. Balance, leg alignment, muscle strength, and muscle coordination are all extremely important factors directly affecting ACL-tear risk. The way a patient or person controls his or her body weight under motion, the way in which he or she bends or straightens the leg, and the way he or she fires or controls muscle activation for any given set of exercises or during sports all affect the ACL-tear risk. Most people with a torn ACL will experience instability, a feeling that the knee gives way or feels loose. This instability commonly results in a reduction in activities, especially sports. More importantly, the instability will usually lead to additional damage to the knee if left untreated.

One of the most common causes of non-contact ACL-tears is ACL reconstruction surgery. Patients who go through ACL reconstruction surgery bear a risk of needing a second knee surgery within two years. Studies have shown up to a 20 to 30% chance of having subsequent knee surgery after having an ACL reconstruction. There are several important parameters that affect injury or re-injury risk. For example, the alignment of the lower extremities relative to the hips is the most important and well documented; however, the degree the knee is bent for jumping and landing activities and absolute muscle strength are also important factors to consider. The variations of ideal alignment, or the degree of knee bend, or muscle strength should be calculated and tracked from the beginning of rehab to the end.

An important way to prevent non-contact injuries is to evaluate and eventually improve neuromuscular efficiency. As defined by the National Academy of Sports Medicine, neuromuscular efficiency refers to the ability of the nervous system to properly recruit the correct muscles to produce and reduce force as well as dynamically stabilize the body's structure in all three planes of motion. This is tied closely to reaction time and muscle memory. For example, neuromuscular efficiency is involved when an individual is pushed or shoved unexpectedly. How quickly the individual regains his or her balance is directly related to neuromuscular efficiency; that is, people with high neuromuscular efficiency will recover from the push very rapidly because the brain and central nervous system, generally, interact with the muscles relatively quickly, while those with low neuromuscular efficiency will take longer to recover or may even fall down. For that reason, people with a low neuromuscular efficiency tend to be more injury prone than those with a higher neuromuscular efficiency. In fact, it is believed that improving one's neuromuscular efficiency may reduce the likelihood of injury or re-injury by as much as 70 percent.

SUMMARY OF THE DISCLOSURE

One aspect of the present disclosure includes a computer-implemented method for facilitating the evaluation of at least one user activity element, wherein the method comprises at least the steps of: receiving, via at least one computing device, at least one user activity event record from at least one sensor; storing, via the at least one computing device, the at least one user activity event record;

and presenting, via the at least one computing device, information about the at least one user activity event record; wherein the at least one user activity event record comprises at least one movement detected by the at least one sensor, wherein the at least one movement is caused by at least one of: an object and a user's body.

Another aspect of the present disclosure includes one or more computer storage media having stored thereon multiple instructions that facilitate the evaluation of at least one user activity element when executed by one or more processors of at least one computing device, causing the one or more processors to: receive at least one user activity event record from at least one sensor; store the at least one user activity event record; and present, via the at least one computing device, information about the at least one user activity event record to a user; wherein the at least one user activity event record comprises at least one movement detected by the at least one sensor, wherein the at least one movement is caused by at least one or more of: an object and a user's body.

Another aspect of the present disclosure includes a system for facilitating the evaluation of at least one user activity element, comprising: at least one computing device operated by at least one user, the at least one computing device being configured to communicate with at least one application server via a communications network; at least one sensor configured to communicate via the communications network and detect at least one user activity event record, wherein the at least one sensor is removably attachable to at least one or more of: an object and a user's body; at least one computational database; and at least one application server configured to communicate, via the communications network, with the at least one computing device, the at least one sensor, and the at least one computational database; wherein the at least one application server comprises: a data receiving means configured to receive data from at least one or more of: the at least one sensor and the at least one computing device, and store the received data in the at least one computational database, wherein the received data is retrievable by the at least one user; a data analyzing means configured to analyze at least one aspect of the received data, wherein at least one form of the data analyzing means comprises a comparison function; and a presentation means configured to provide the received data to the at least one user, including any analysis that has been performed on the data, by presenting the data to the at least one user via the at least one computing device.

Further features and advantages of the present disclosure, as well as the structure and operation of various aspects of the present disclosure, are described in detail below with reference to the accompanying drawings.

DETAILED DESCRIPTION

Figure 1:
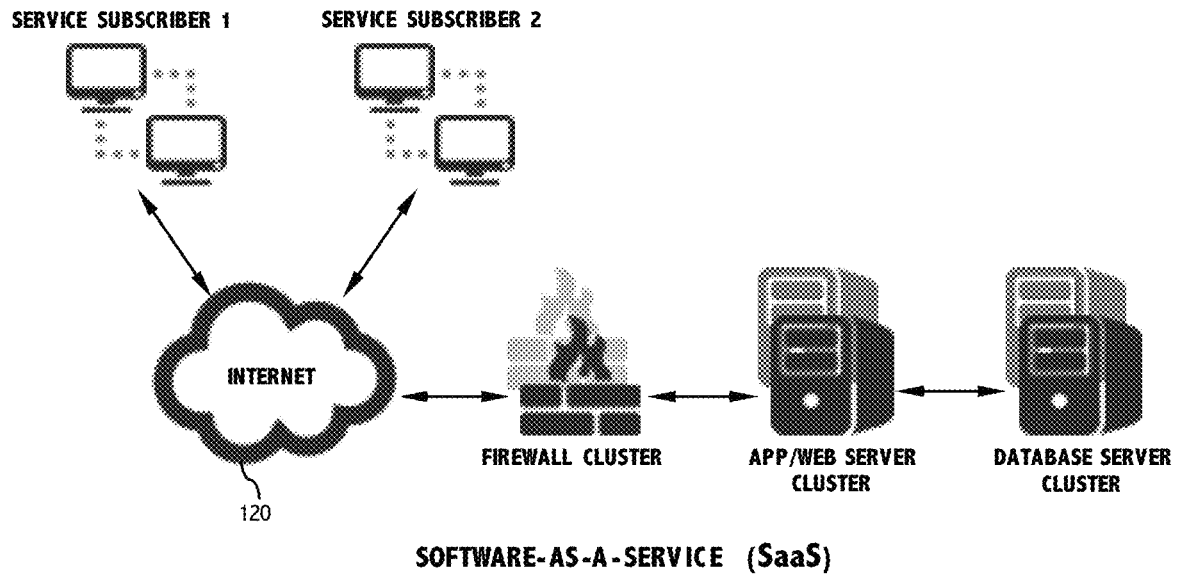
FIG. 1 shows a block diagram of a system implementing the present disclosure on a Software-as-a-Service (SaaS) platform, according to one aspect of the present disclosure.

There exists a need for systems, methods, and computer program products that monitor and assess the location of and forces transferred to various joints, muscles, and limbs and their relative positions at each and every moment during normal daily activities, during training loads of an exercise, or during competitive or high intensity athletic endeavors, to mitigate and reduce the risk of injury as well as to track fitness performance elements. Systems, methods, and computer program products that measure and improve neuromuscular efficiency for an individual are also desired.

Aspects of the present disclosure meet the above-identified needs by providing systems, methods, and computer program products which facilitate the ability of a user to receive quantified information as to the user's likelihood of incurring an injury and/or receiving quantified information regarding various aspects of the user's overall fitness levels, including neuromuscular efficiency. Such information may be based on objective as well as subjective data. The information provided to the user by the systems, methods, and computer program products of the present disclosure may assist the user in determining if the user is prone to injury, has adequately recovered from an injury, and/or how well the user ranks in various fitness performance categories, including for example neuromuscular efficiency, and thereby helps the user determine where to focus improvement efforts.

In one aspect, the systems, methods, and computer program products of the present disclosure utilize at least one sensor in order to capture objective motion information related to a user while the user engages in various tasks and/or exercises. Such sensors may be attached directly to the user's body via, for example, various straps and braces, or the sensors may be incorporated with various objects or proxies the user may engage with while moving, including gym equipment, sports equipment, and the like.

Subjective information may also be obtained from the user, such as by the user completing a questionnaire, for example. The questionnaire may comprise various questions that relate to the user's strength or weakness levels, pain levels, confidence after an injury, discomfort, medical history, and other factors that may be relevant to the user's performance, recovery, and/or goals.

Information captured by the sensors and received from the questionnaire, as well as relevant information received from other sources, may be received and analyzed by one or more software applications accessible by a user computing device. These applications may be used to, among other things, provide quantified, measurable, and calculable information regarding the user's likelihood of getting injured, rehabilitation progress after an injury, and/or ranking with regard to health, fitness, and/or performance categories.

While specific exemplary embodiments are discussed, embodiments are not intended to be limited to the specific terminology so selected. A person skilled in the relevant art(s) will recognize that other components and configurations may be used without parting from the spirit and scope of the embodiments. It is to be understood that each specific element includes all technical equivalents that operate in a similar manner to accomplish a similar purpose. The examples and embodiments described herein are non-limiting examples.

The present disclosure relates to systems, methods, and computer program products for monitoring and assessing location of and forces transferred to various joints, muscles, and limbs and their relative positions at each and every moment during normal daily activities, training loads of an exercise, or a competitive or high intensity athletic endeavors. Aspects of the present disclosure have a variety of great usages in different industries and fields. A great exemplary usage would be in monitoring injured anterior cruciate ligament (ACL) recovery processes to determine the threshold for release to unrestricted activities, which should lessen the risk for repeat injury. As further explained below, a Body Area Network captures objective data from sensed measurements. Along with objective data, multifactorial questions depending on person, sport, time of sport season, etc. are used as subjective data for a questionnaire prior to a treating physician's clearance date and for setting goals or restrictions, as well as for assisting individuals in setting training performance goals.

The systems, methods, and computer program products of the present disclosure may also be used to measure a user's neuromuscular efficiency and help the user make improvements thereto.

Referring now to FIG. 1, a block diagram of a Software-as-a-Service (SaaS) platform offering services embodying various aspects of the present disclosure is shown. SaaS is a software licensing and delivery model in which software is licensed on a subscription basis and is hosted centrally or distributed. The SaaS can offer a wide variety of services to subscribers including, but not limited to, health, financial, cyber-security, industrial, transportation, manufacturing, and construction services. The SaaS platform comprises an Application/Web Server Cluster of one or more servers, which communicates with a Database Server Cluster of one or more databases.

The SaaS platform can be used to provide application services offered to multiple service subscribers. For example, a first and a second service subscriber can each offer independent application services to individuals or participants in an institution or organization over the Internet via a firewall Cluster of one or more firewalls. One such SaaS can be implemented on a cloud to serve various industries such as medical, fitness, financial, multimedia, transportation, logistics, or etc.

Generally, the network over which the present disclosure is implemented comprises a plurality of privately or publicly connected nodes, comprising one or more processor nodes, or servers or clusters of servers and/or nodes, that are enabled to exchange information over one or more links. Exemplary networks comprise any one or more of WANs, LANs, PANs, Internet 120, as well as ad hoc networks such as Bluetooth® (a wireless technology standard standardized as IEEE 802.15.1) or Extranets. The Internet 120 is a collection of interconnected (public and/or private) networks that are linked together by a set of standard protocols to form a global, distributed network. A node comprises one or more processor units (software or hardware, or virtual nodes) and/or devices located anywhere in the network that processes information and/or performs an attributed function. Any node or any component with a node can be virtualized in hardware or software. Different types of nodes can include a receiver node, which receives information, a processor node, which processes information, and a transmitter node, which transmits processed information. Examples of nodes include server nodes, client nodes, computer nodes, processor nodes, communication nodes, work stations, PDAs, mobile devices, entry nodes, exit nodes, user interface nodes, accounting nodes, administration nodes, content delivery nodes, selection nodes, sensor nodes, wired nodes, wireless nodes, and etc.

In one embodiment, the system of the present disclosure comprises one or more servers configured to interface with a plurality of user devices over the network. The plurality of user devices can be one or more first user devices and one or more second user devices operating individually or in groups or sub-groups. The nodes of the system can be connected to each other according to any suitable network model, including but not limited to client server models as well as hierarchical or distribution models. A link comprises any medium over which two nodes may communicate information with each other. Exemplary links include, but are not limited to, wired, fiber, cable, or wireless links (e.g., Bluetooth®, UWB, USB, etc.). A communication channel comprises any channel used with a link for delivery of content, which can include data obtained from nodes, applications executing in nodes or devices, objects (e.g., vehicles, people), or sensors.

Figure 2:
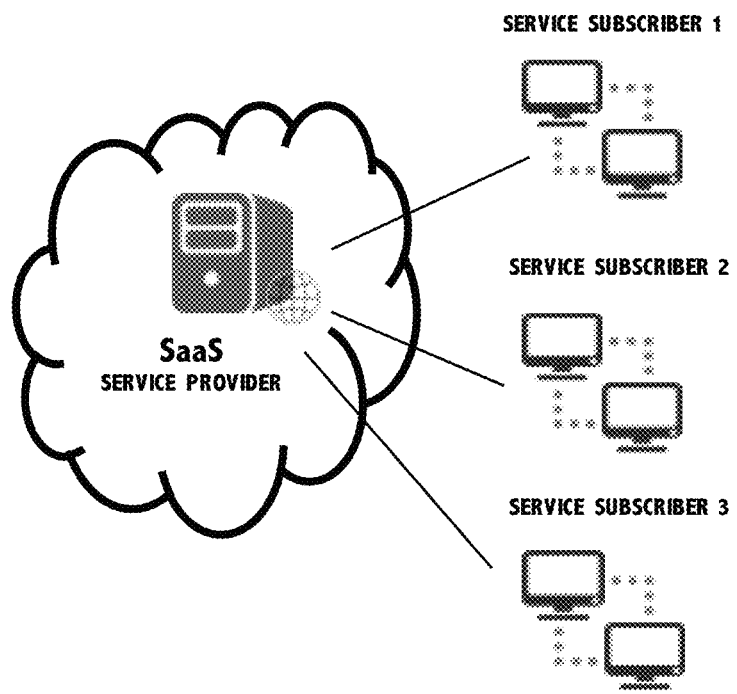
FIG. 2 shows an exemplary embodiment of the system shown in FIG. 1 implemented as a cloud service subscribed by a plurality of service subscribers, according to one aspect of the present disclosure.

FIG. 2 shows an exemplary system of FIG. 1 implemented as a cloud service subscribed by three service subscribers. Under one arrangement, each service subscriber can be paired with another service subscriber within the SaaS for collaboration purposes. That is, Service Subscriber 1 can be paired with Service Subscriber 2 and Service Subscriber 2 can be paired with Service Subscriber 3, while Service Subscriber 1 is also paired with Service Subscriber 3. Under a premium subscription level, anyone of the service subscribers can deploy a service in-house as an enterprise solution for collaboration management, yet seamlessly communicate with the SaaS platform for exchange and collaboration with other collaboration service subscribers.

Figure 3:
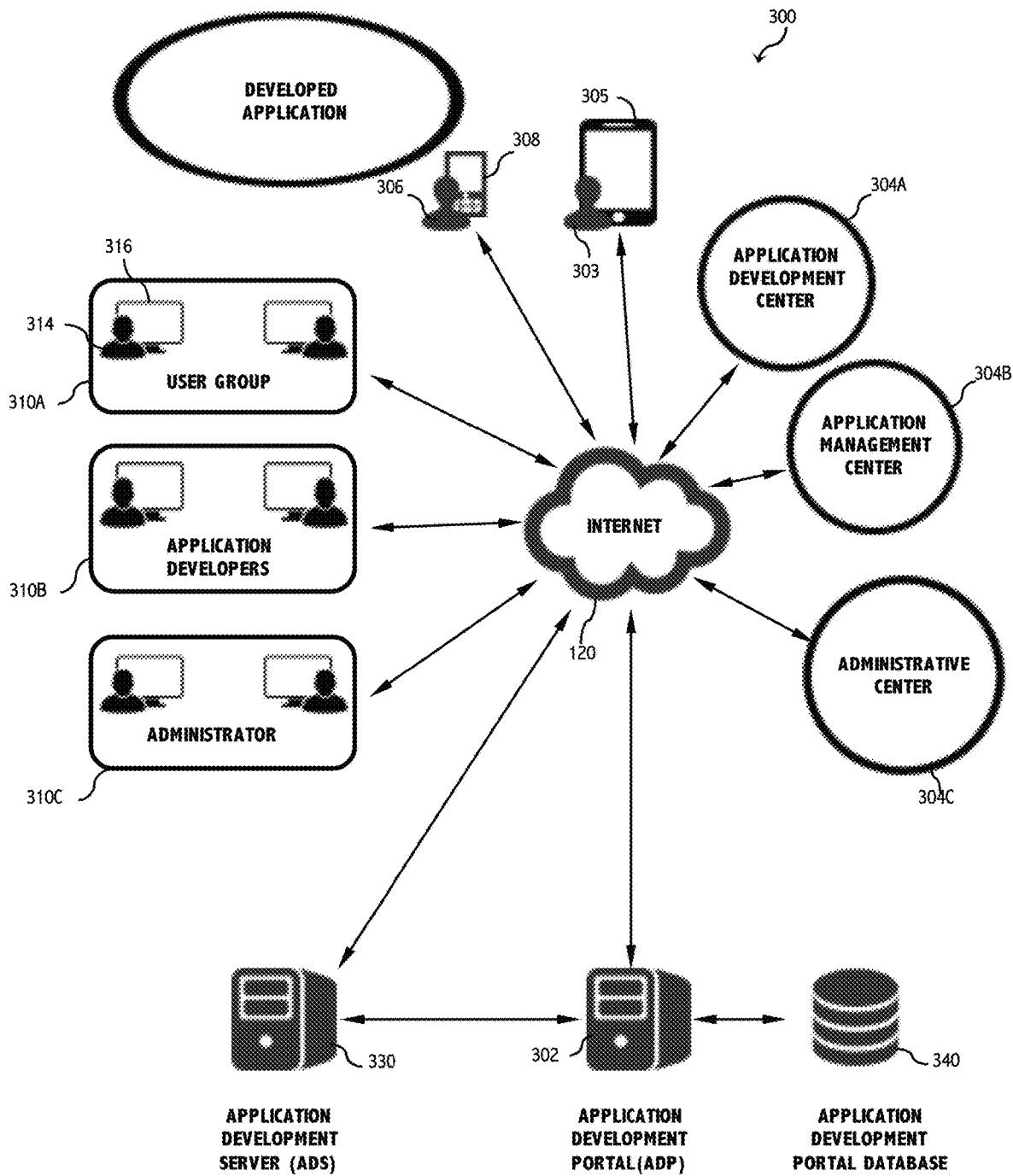
FIG. 3 shows an exemplary block diagram of an application development system according to one aspect of the present disclosure.

FIG. 3 depicts an exemplary block diagram of an application development system 300 that develops various applications for users. An application development center 304A, an application management center 304B and an administrative center 304C are connected to an application development portal (ADP) 302 through a network, such as the Internet 120. The ADP 302 provides a gateway between the user devices 305, 308, 316, the application development support centers 304A-C, and the application development system (ADS) 330 through the network 120. The ADS 330 provides the necessary user interfaces for application developers, reviewers, users, administrators and other participants to communicate with one another to, for example, allow application development users/participants to interact with each other. Such application development may take place over cloud systems.

Participants or users can use the developed applications with different service subscribers, where a first service subscriber offers a first application or solution to a first group of users/participants and a second service subscriber offers a second application for a second group of users/partici-pants. Users of developed applications can be individual users 303 or 306 (mobile devices 305 and 308), a user group 310A (or a user sub-group) of users 314 (fixed workstation 316). Users of the system can also be application developers 310B as well as administrators 310C and any other person that uses the system of FIG. 3 for developing or using applications. Such users can be professionals, developers, technical support personnel, accounting personnel, experts or any other participant in an application. The users 303, 306, 314 at the user devices 305, 308, 316 may include patients, doctors, health professionals, consultants, suppliers, application developers, content developers, financial institutions, insurance companies, etc. Alternatively, the user may be a responsible authority registered at the application development center 304A, the application management center 304B, or the administrative center 304C.

The ADP 302 provides access to an application portal database 340, which stores user information for all participants/users enrolled or associated with each application development process. The ADP 302 provides means for participants to log onto the application development server 330 with a user ID and password. Based on the access privilege associated with the user ID, the ADP 302 may authenticate the participant as a developer, an administrator, a reviewer, a health professional, a teacher, a student, or any other type of user, etc. Finally, the ADP 302 synchronizes the information stored between the ADS 330 and the support centers 304A-C. Through the environment created by the system and method of the present disclosure, an application can be served to users in a centrally or distributed hosted manner, for example on a subscription basis or other for-profit or non-profit arrangement.

Figure 4:
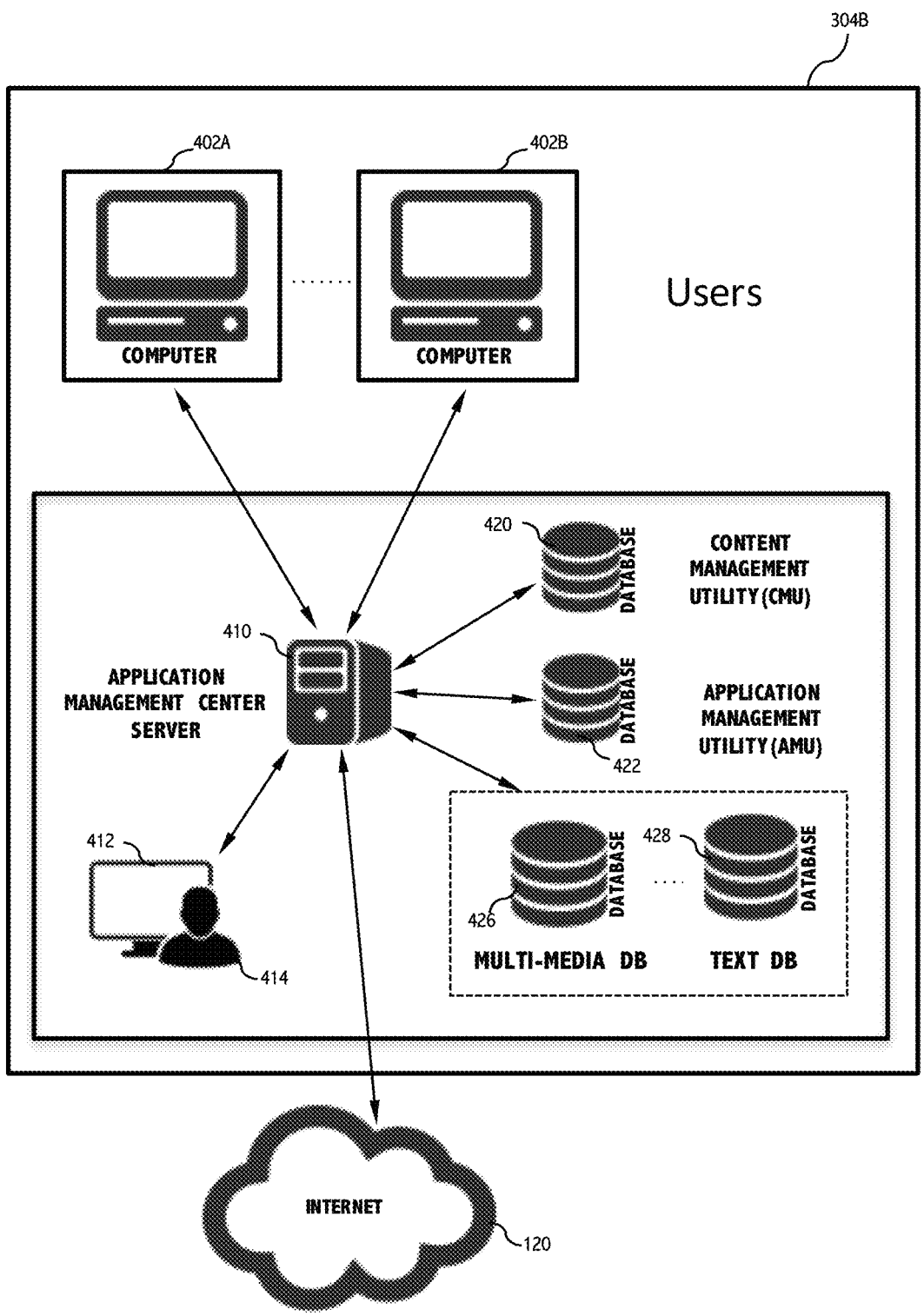
FIG. 4 shows an exemplary block diagram of an application management center, according to one aspect of the present disclosure.

FIG. 4 depicts an exemplary block diagram of the application management center 304B in the application development system 300 of FIG. 3, which is managed and maintained by one or more administrators and accessible by those participants who are involved in the application development process, namely application and content developers. The application management center 304B is used by application/content developers and administrators. The application management center includes an application management server 410 providing connectivity to the Internet 120, and also a system administrator 414 who monitors and administers the local server 410 through a workstation 412.

The application management server 410 executes an application management utility and a content management utility that provides the platform for storing content, which can include multi-media and non multi-media content, examples of which are data obtained from nodes, such as developed content and application materials, sensor information, multi-media information, and etc.

Figure 5:
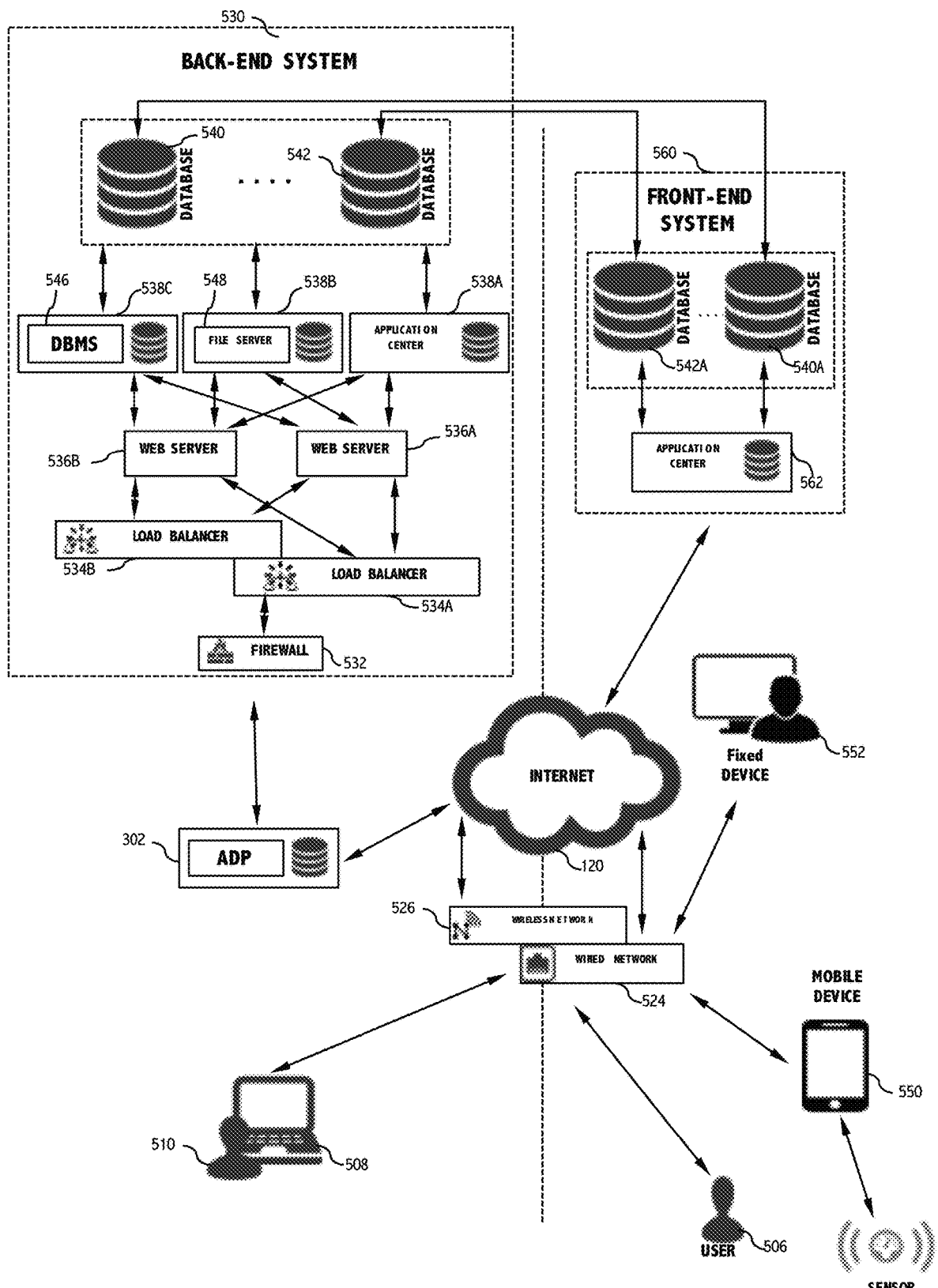
FIG. 5 shows an exemplary block diagram of the operation layers of a system, according to one aspect of the present disclosure.

FIG. 5 shows an exemplary block diagram of the operation layers of the system that implements the present disclosure on a developed application for a service subscriber. According to this embodiment, the system includes a back-end system 530 and a front-end system 560. The front-end system 560 provides user interfaces to subscribed service users and participants for accessing and using developed applications. The back-end system 530 is used for system administration, billing, marketing, public relations, etc.

The front-end system 560 allows user access to application center 562, which accesses back-end databases 542 and 540. The front-end system 560 provides the participants interactive access to users and user groups sessions via user devices 550 and 552. In one embodiment, the user device 552 is a fixed device and the user device 550 is a mobile device. The mobile devices can be associated with processors, sensors, objects, people, animals, vehicles, etc. The mobile devices can be smart phones, mobile objects, tablets, notebooks, lap tops, etc. In one embodiment, the mobile devices execute location aware applications which allows them to be located through wireless geo-location capabilities, such as GPS or assisted GPS with cellular, UWB, infrared, etc. The mobile devices are also equipped with ad hoc networking capabilities, such as the Bluetooth®, NFC, RFID, etc., to communicate with external devices, such as sensor, multi-media, storage, as well as remote processing nodes.

Via the Internet 120 or through a wired network 524 and/or a wireless network 526, the users interface with the front-end and back-end systems 560 and 530. In the back end, the user devices 508 are connected to the ADP 302 via a network, which may be a private or public network. In an exemplary embodiment, the user devices execute a network access application, for example, but not limited to, a browser or any other suitable application or applet, for accessing the back-end system 530 or the front-end 560, depending on defined access privileges which may be subject to multiple levels of administrative privileges under multiple levels of access control, according to, for example, various EAL levels. The users 510, 552, or 550 may be required to go through a log-in session and multiple levels of authentication before entering the system.

In the exemplary embodiment shown in FIG. 5, the back-end system 530 includes a firewall 532, which is coupled to one or more load balancers 534A, 534B. Load balancers 534A-B are in turn coupled to one or more web servers 536A-B. The web servers 536A-B are coupled to one or more application servers 538A-C, each of which includes and/or accesses one or more databases 540, 542, which may be central or distributed databases. Web servers 536A-B, coupled with load balancers 534A-B, perform load balancing functions for providing optimum online session performance by transferring subscribers, participants, users, developers, or administrators requests to one or more of the application servers 538A-C. The application servers 538A-C may include a database management system (DBMS) 546 and/or a file server 548, which manage access to one or more databases 540, 542. In the exemplary embodiment depicted in FIG. 5, the application server 538A and/or 538B provides applications to the participants 506, 510, 552 which includes electronic interfaces, application material, participant profiles, etc. Some of the content is generated via code stored either on the application servers 538A and/or 538B, while some other information and content is retrieved along with the necessary data from the databases 540, 542 via application server 538C. The application server 538B may also provide users 506, 510, 552 access to executable files which can be downloaded and installed on user devices 550, 508, 552 for creating an appropriate virtual application environment, with or without commercial, branding and/or marketing features that are tailored for a particular application, a user or user groups.

The central or distributed database 540, 542, stores, among other things, the content and application material deliverable to the participants. The database 540, 542 also stores retrievable information relating to or associated with various types of participants, developers, administrators, user groups, health professionals, teachers, students, application development center, application management center, the administrative center, user profiles, billing information, schedules, statistical data, progress data, social network data, user attributes, participant attributes, developer attributes, mass collaboration data, ranking data, compliance data, certification data, billing rules, third party contract rules, government requirements, etc. Any or all of the foregoing data can be processed and associated as necessary for achieving a desired objective associated with operating the system of the present disclosure. For example, statistical data related to conditions, user progress, schedules, and so on.

Figure 6:
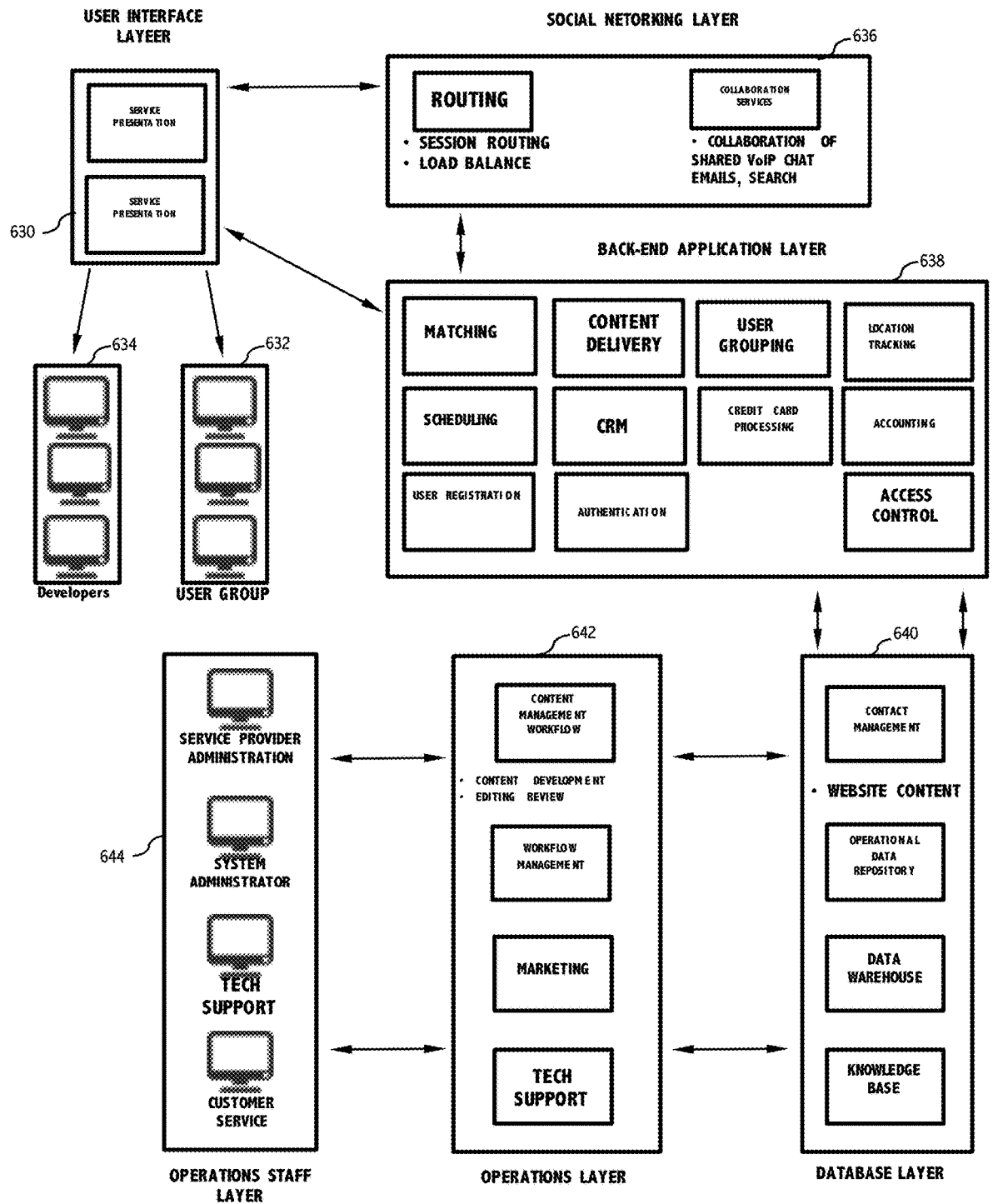
FIG. 6 shows an exemplary block diagram of a service, serving a developed application to subscribers, according to one aspect of the present disclosure.

FIG. 6 depicts an exemplary functional block diagram that implements a service according a developed application to users or user groups (workstations 632) and administrator workstations 634. Each workstation can be a node connected to the system from any location. Various application program layers include social networking layer 636, user interface layer 630, a back-end application layer 638, a database layer 640, an operations layer 642, and an operations staff layer 644. Each layer, or any of its components, can run on any suitably configured node, including servers or workstations, anywhere in the system in a central or a distributed manner.

The user interface layer 630 is responsible for interfacing with participants, reviewers, user groups, developers, and administrators, amongst other users. The user interface layer 630 receives input from multiple user devices or any other node associated with the system, including but not limited to processor, receiver, transmitter, sensors, or nodes associated with social networking services, third-party application development services, etc. The user devices, for example, workstations 632 and 634, are equipped with keyboards, mouses, pointers, displays, pen-based tablets, audio headsets, speakers, cameras, media players, etc. In this way, the user interface layer 630 can communicate text, image, sensor, video, and audio information with the nodes. Communication includes both the receipt and transmittal of information. In one embodiment, participants, users, developers, administrators, and/or experts possess respective access rights that are verified via access control and authentication processes. For example, when a participant logs in, the system provides the necessary rights and privileges for accessing the development system. The back-end application layer 638 may also manage content delivery, users, and application development item matching, as well as mass collaboration scheduling and billing functions. The social networking layer 636 allows collaboration amongst the participants, e.g., team participants, users, and application developers. The social networking layer 636 provides collaboration tools such as chat, VoIP, and video conferencing functions that may be required in an environment for individual users or group of users.

The database layer 640 may manage information storage functions related to user, content, or application developing environments, information and data, including textual documents, multi-media content, digital content, and other knowledge base information. The database layer 640 can also be a repository for operational data including the participants, schedules, ranking results, and selected content items. Data warehousing functions and statistical analysis of reviewer ranking data against pre-defined satisfaction criteria may also be performed by the database layer 640. The database layer 640 may also manage the knowledge base comprising technical support and customer service information.

The operations layer 642 may provide content and application management workflow, including adding content, editing, and reviewing the developed content and application using the system and method of the present disclosure. The operation layer 642 may also manage marketing and CRM (customer relationship management) workflow. This layer may also provide for lead/prospect follow-up functions, technical support problems, and product inquiries. The operations layer 642 may interface with the operational staff layer 644 that comprises personal tech support, customer service, service subscriber, which itself may be a service provider having its own service provider administration, service administrator, and analyst information. The operations layer 642 also may provide for routing of information over the network for applications.

Figure 7:
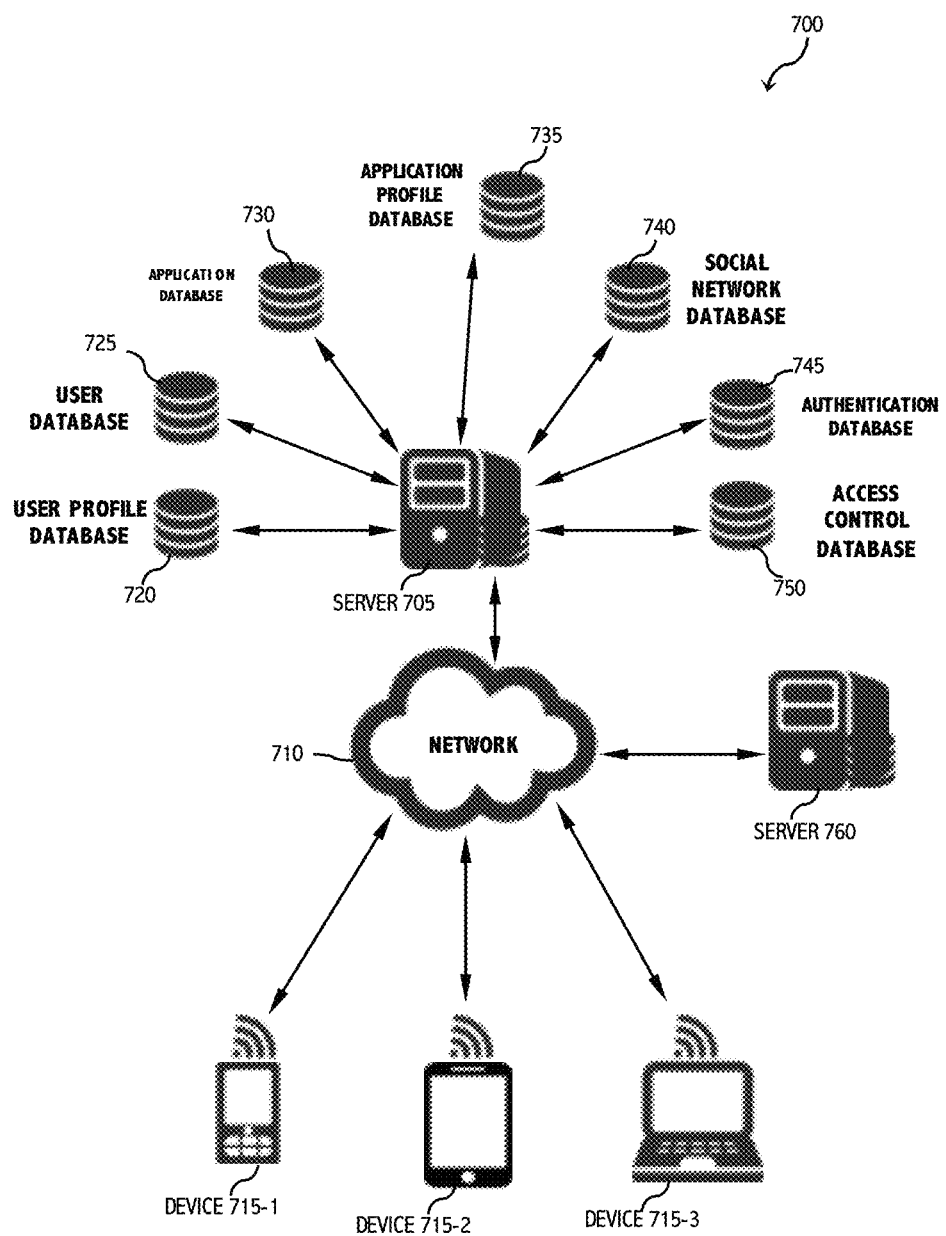
FIG. 7 depicts an exemplary diagram that implements authentication, social networking, and profiling into the system shown in FIG. 1, according to one aspect of the present disclosure.

FIG. 7 is a diagram that implements authentication, social networking, and profiling into the system of FIG. 1. In one embodiment, users of devices 715-1 through 715-n may register within a particular system and may connect to a network 710 (e.g. the Internet). Each of devices 715-1 through 715-n may be a computer, a workstation, a mobile device, a PDA, an iPad, a laptop computer, or etc. A server 705 may be maintained in a social networking system 700 and may also include a server 760. Server 760 may include any combination of features of server 705. Server 760 may also be connected to the other parts of a social networking system 700 through network 710. Server 760 may be located on the same network as server 705 or on a different network as server 705. Server 760 may run or operate other instances the software used to provide the online collaboration system. Server 760 may run or be operated by other institutions or entities, either foreign or domestic. Server 760 may run or be operated by the same institution or entity but in separate locations, either foreign or domestic.

Server 705 may be connected to or include a number of databases, including a user profile database 720, a user database 725, an application database 730, an application profile database 735, a social network database 740, an authentication database 745, an access control database 750, or any combination thereof. The user profile database 720 may store, for any user, content, weekly schedules, assignments, resources, due dates, discussions, reflections, content summaries, content reviews, tests, any other content or application material information, or any combination thereof.

User database 725 may store any information about users using the system. User database 725 may store an inventory of all users that are affiliated with a particular case, application, institution, or company. In one embodiment, such users are associated with network addresses, e.g., IP addresses, that may be stored in a user's profile. User database 725 may store information about the users' names, user specific data and content, locations, addresses, information about the users entered by the users or developers or administrators, activities and interests of the users, education of the users, work experiences of the users, pictures of the users, etc., or any combination thereof.

Application database 730 may store any information about the application offered by the system 700. Application database 730 may store content and application names, identifiers, numbers, descriptions, health professionals, schedules, enrollments, past content, future content, number of users allowed to participate in a content or application, application structure, application or content prerequisites, user group, or any combination thereof.

Application profile database 735 may store information about users, or application, including information about users according to their role. For example, Application profile database 735 may store information about programs the patients have completed, activities the patients have completed, examples of health products the patients have completed, evaluations, rankings, or any combination thereof.

Social network database 740 may store social networking information about the users of the system. Social networking information may include contacts of the users to which the users are connected, circles of the users, chat connections of the users, chat histories of the users, communities of the users, contents and applications associated with the users, or any combination thereof. As used herein, a circle of a user means a set of other users associated with a user in the system. In one embodiment, a user's circles may be set by the user. As used herein, a community of the user may include any group or association of which the user is a part as identified by the system. Communities are different from contacts and circles because communities cannot be directly modified by users. Communities may be disbanded once a program or application ends, or past communities may be maintained. Social network database 740 may also store any other information related to the social networking information.

Authentication database 745 and access control database 750 may store security, access, or authentication information for the system. Security or authentication information may include usernames of the users, passwords of the users, security questions used for verifying the identity of the users, answers to security questions, which parts of the system the users are able to access, or any combination thereof.

Figure 8:
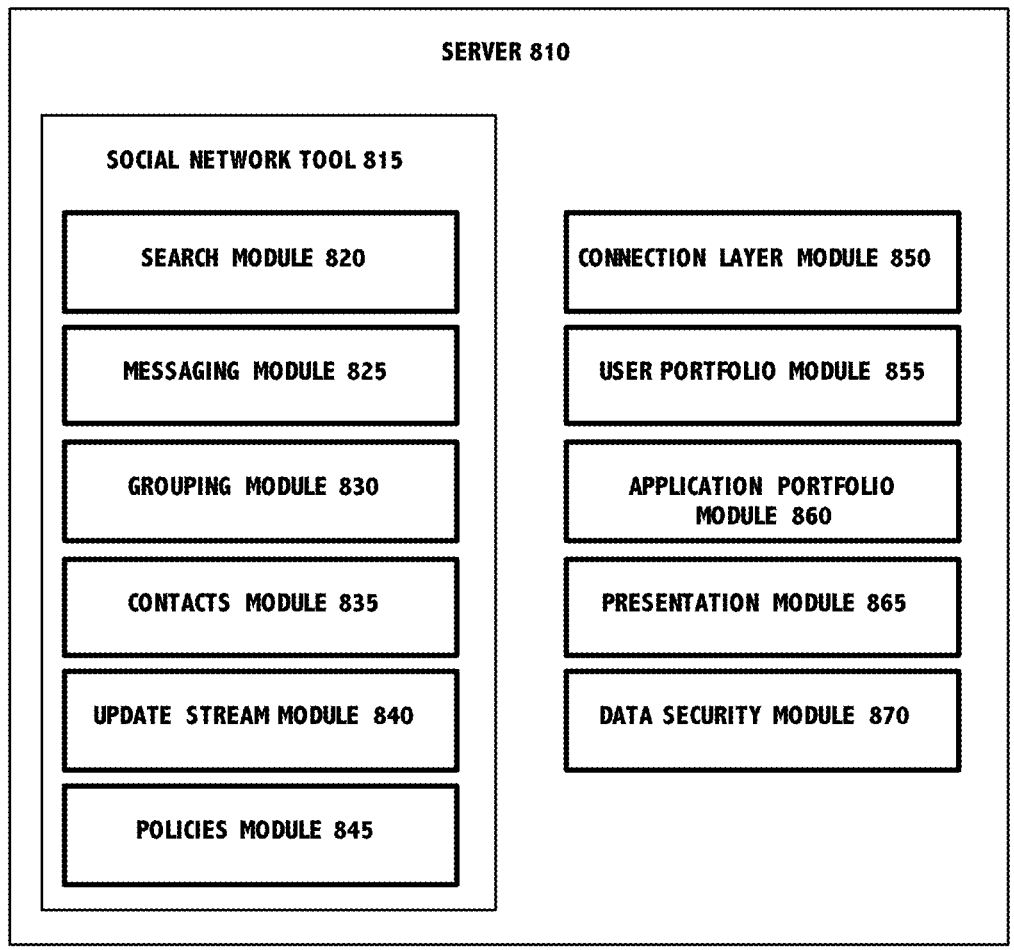
FIG. 8 is a functional block diagram of the social networking system, according to one aspect of the present disclosure.

FIG. 8 shows physical topology of a site comprising computing servers, such as industry standard x86 servers that run under the control of one or more server operating systems, such as Windows, Linux, or VMware that create virtual or non-virtual environments. A number of similarly configured x86 servers can be grouped together with connections to the same network and storage subsystems to provide an aggregate set of resources. Enterprise storage, comprising Fiber Channel SAN arrays, iSCSI SAN arrays and NAS arrays, is used to meet different storage needs. Sharing the storage arrays between (by connecting them to) groups of servers via storage area networks allows aggregation of the storage resources. Server 810 may include a social network tool 815, a connection layer module 850, a user portfolio module 855, an application portfolio module 860, a presentation module 865, a data security module 870, or any combination thereof. Social network tool 815 may include a search module 820, a messaging module 825, a grouping module 830, a contacts module 835, an update stream module 840, a policies module 845, or any combination thereof. The modules may provide the functionalities as further described below.

The Monitoring System

Figure 9:
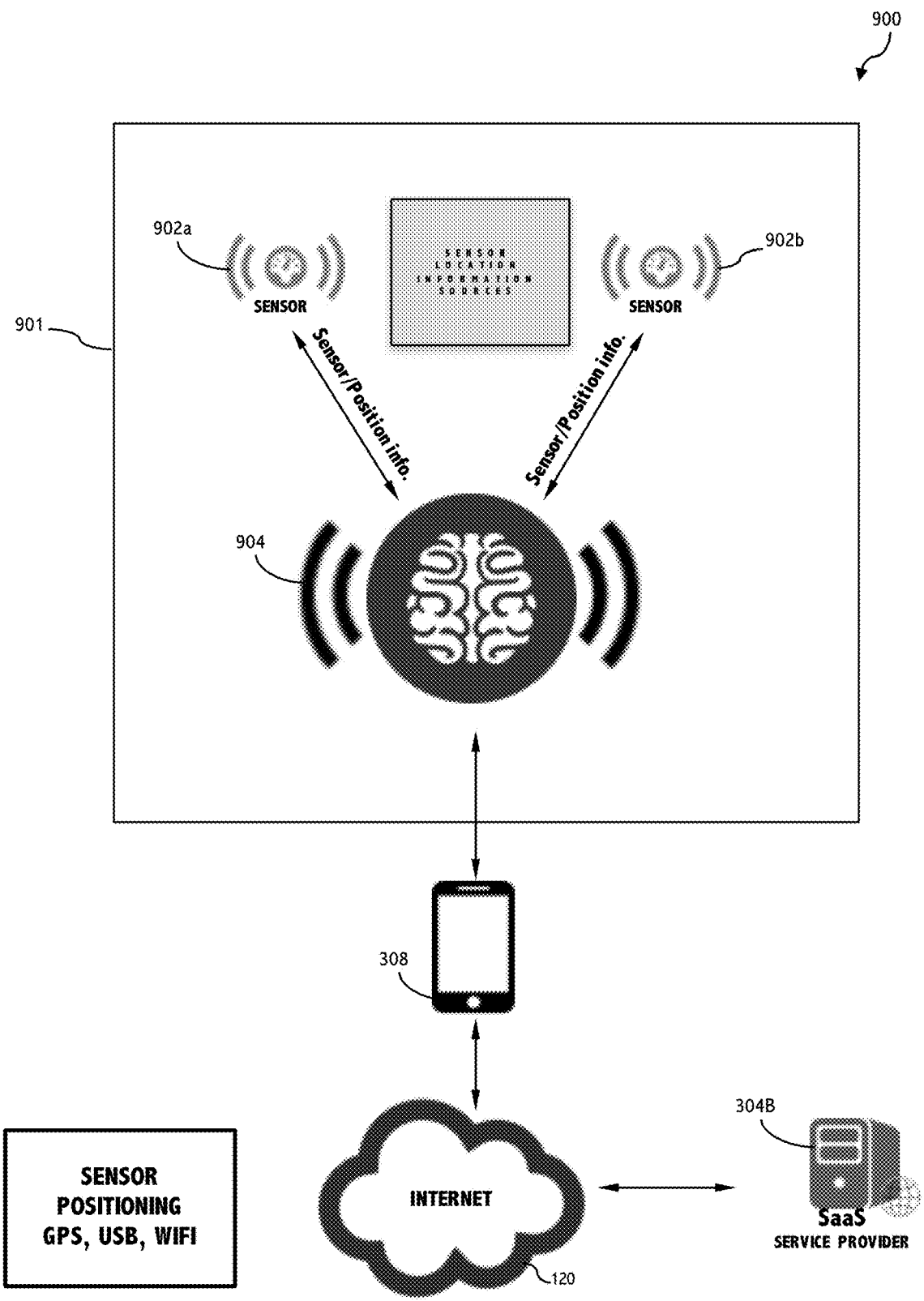
FIG. 9 shows a block diagram depicting one application, according to one aspect of the present disclosure.

FIG. 9 shows an exemplary block diagram depicting one application in the system 900. The monitoring system 901 collects data regarding the position and movement of body parts attached to any joint using a plurality of portable sensors 902 (shown as sensors 902a-b in FIG. 9), and brain node 904. In one embodiment, the monitoring systems is oriented about a user's body as a wearable device including suitable attachment mechanisms, e.g., straps, etc. Motion and position sensor devices/nodes 902 in the wearable device transmit sensor information via an ad hoc network such as Bluetooth® to a brain node 904, which communicates with a mobile user device 308 via a wireless link. In this way, the movement and position data of specific body parts are received by the brain node 904, where the data is stored, localized, and categorized based on application requirements, such as position or sensor signal, or timing, etc. Brain node 904 has a two-way wireless communication with user device 308 and transmits the data to the user device, which in turn transmits the same data via Internet 120 to the application management center 304B, where the data is processed according to a specific application.

In some aspects, every sensor 902 is a brain node 904. That is, in such aspects, every sensor 902 has a two-way wireless communication with user device 308 and transmits data to user device 308, which in turn transmits the same data via Internet 120 to application management center 304B, where the data is processed according to a specific application.

In some additional aspects, sensor devices 902 and/or brain nodes 904 are not comprised as wearable devices, but rather are configured to be removably or permanently attached to one or more objects, such as pieces of gym equipment or other activity devices.

In one embodiment, the system of the present disclosure will help healthcare providers, such as heath experts, doctors, therapists or individuals to assess and calculate a fitness index for injury risk to any body joint by processing the data collected in the brain node 904. The application management center 304B processes this data along with other content such as subjective data gathered from a questionnaire using an algorithm to create a BaziFIT score which will allow health care providers such as physicians or physical therapists working with an injured person to determine when the person can resume unrestricted activities with lessened risk for repeating the same injury and determine the best rehabilitation methods to meet the end goal(s) of the user.

Accordingly, a wearable sensor unit includes a brain node 904, in some aspects, and a plurality of motion and position sensor devices 902. Sensor devices 902 can be any device that permits position or motion measurements. Positions or motions can either be absolute or relative ones (e.g., displacement sensor). Sensors 902 may be linear, angular, or multi-axis, accelerometer, gyroscopes, magnetometers, capacitive, ultrasonic, current, hall effect, inductive, Doppler, laser, transformer, displacement transducer, photo-diode, piezo-electric, potentiometer, proximity, rotary, etc. Brain node 904 is a central sensor information-capturing node, which aggregates and stores data received from itself and/or from motion and position sensor devices 902. The data that brain node 904 receives may include information regarding the position and motion of sensor devices 902. Brain node 904 synchronizes the timing for receiving position information from sensor devices 902. Sensor signal time synchronization can be based on reference timing data exchanged over a wireless link. In this way, brain node 904 receives data from sensor devices 902 located around a specific body joint at the same exact time. Additionally, brain node 904 categorizes the data it receives before transmitting it to user device 308. This categorization may be according to the time as well as the location of the data received, or any other categorical index defined by the application.

According to still another embodiment, the system uses geometry and math and some basic assumptions to calculate muscle size electronically and also range of motion. In one example, shown in FIG. 9, such calculations are made after a wearable brace containing two sensor devices 902 with positioning capability, e.g., RF, UWB or optical positioning that provides distance information between the nodes. In this way, the distance from the center of the tibia (based on anthropomorphic calculations) of the node below the knee, the center of rotation of the knee can be determined. Once the center is calculated, estimates of the distance anterior to this center of rotation can be used to determine the width of the thigh at the top of the brace. Also, mobile devices or sensors 902 can be associated with location information sources, such as GPS, Wi Fi, cellular, AGPS or UWB etc. for determining sensor positions relative to each other.

Figure 10:
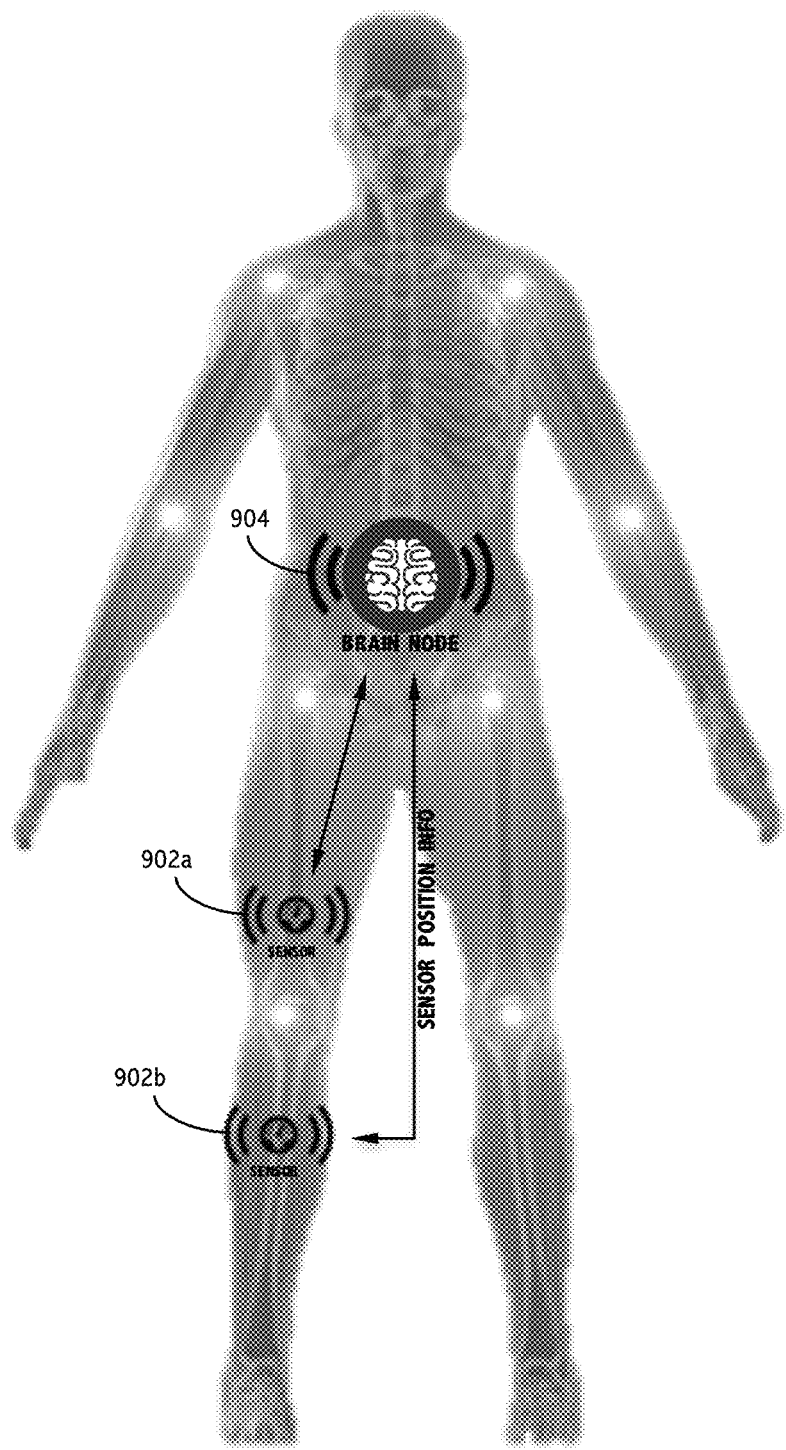
FIG. 10 shows a plurality of mobile sensors affixed to a user, according to one aspect of the present disclosure.

FIG. 10 shows an exemplary depiction of the monitoring system 901, with a plurality of portable sensors 902 (shown as sensors 902*a*-*b* in FIG. 10) that are capable of being affixed to a user's body via a wearable housing unit, which facilitates coupling to specific body parts of the user (such as directly above and below the knee joint) without hindering the user from performing typical user activities (such as walking, stretching, or bending a joint). In this embodiment, brain node 904 is affixed to the lower portion of the back of a user's shirt and the motion and position sensor devices 902 are located immediately above and below a users knee joint affixed to pants or leg sleeves, for example via straps or other wearable mechanism. In this embodiment, sensor devices 902 detect the position and motion of the joints, and size of muscles. Such sensor information is processed at a remote server as a user performs activities for measurements of alignment, range of motion, and equilibrium of the knee, for example. In other application, sensors 902 can be positioned around any body part, e.g., shoulder, heart, bone, etc., to sense position and motion, temperature, heart rate, breathing rate, muscle size, etc.

In one example application, the sensor information is processed to determine alignments of bones directly attached to a joint. Such determined alignments are used for determining a joint's injury risk. In the medical profession, the terms Valgus and Varus refer to an angulation within the shaft of a joint. Valgus refers to a deformity where an anatomical part is turned outward and away from the midline of the body and Varus is where an anatomical part is turned towards the midline of the body.

Figure 11:
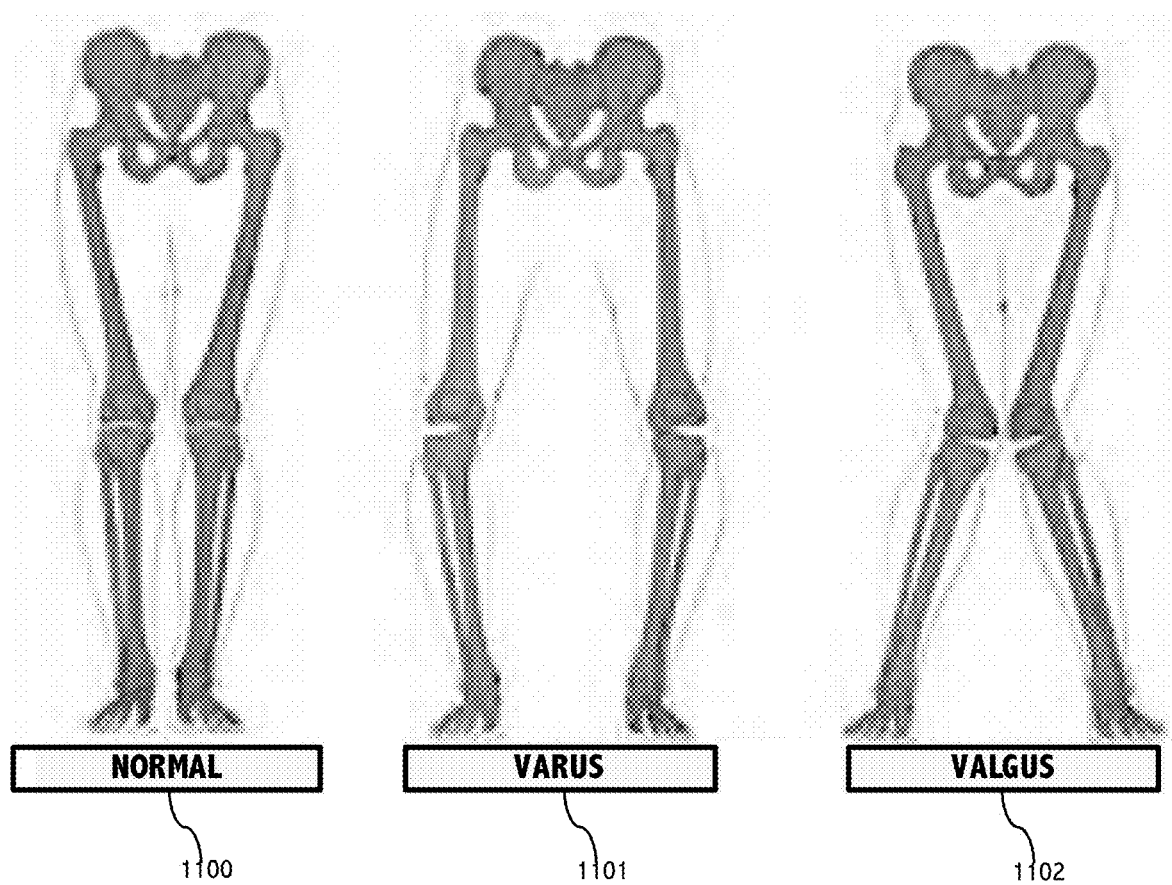
FIG. 11 shows skeletal images of various knee joint alignments, according to one aspect of the present disclosure.

FIG. 11 shows skeletal images of a normal knee joint 1100, a knee joint displaying varus 1101, and a knee joint displaying valgus 1102. A valgus alignment of the knee joint has been shown to be associated with an increased risk of Anterior Cruciate Ligament sprain or tear. In one example, the system determines variations from the normal or "ideal" position of the alignment of the knee joint through the data collected from sensor devices 902. The variation of a user's joint alignment from the normal is one of the factors used in determining a user's joint injury risk upon resuming unrestricted activities.

The range of motion of a joint is another important parameter for determining the likelihood and risk of injury to the joint. For example, the range of motion of a knee joint is the degree a knee bends during jumping or landing activities (such as jumping from about a foot in the air to the ground). People whose knees are less flexed or bent and therefore straighter during a jump, or when landing on their feet, have a greater risk of injury to their knee joint.

Figure 12:
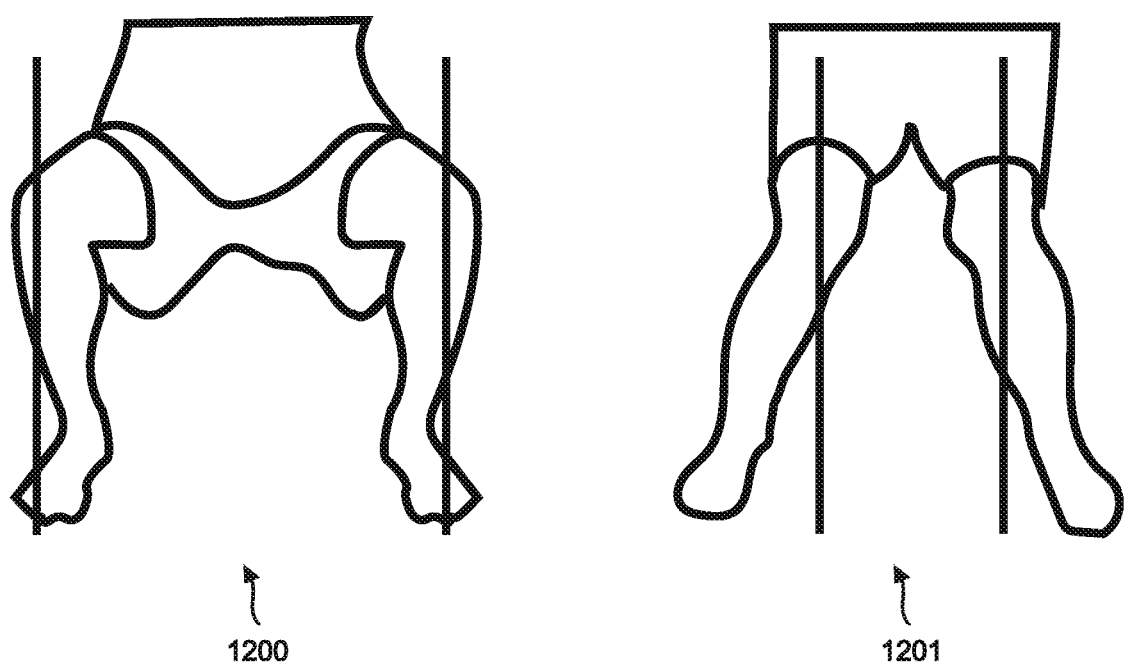
FIG. 12 shows images of different users with different range of motions in their knees according to one aspect of the present disclosure.

FIG. 12 shows images of different users with different range of motions in their knees. User 1200 has more knee joint range of motion than user 1201, which can be seen from the amount each knee is bent. In one embodiment, sensor devices 902 located above and below the knee provide information about the range of motion of a joint. Such range of motion can be determined based on the movement or positions of the sensor devices in reference to each other. For example, if two sensor devices 902 are placed above and below the knee joint, the range of motion of the knee, which is equivalent to how much the knee bends is based on the relative position of the two sensor devices from each other at different times when the knee bends. In an example where a user is performing physical therapy after surgery due to an injury, the range of motion of the user's joint can be measured during every physical therapy session in order to track progress of the users joint and how much that joint has returned or recovered to a normal range of motion. The application described herein is just one example application that allows for remote monitoring of joint movement. The sensor information can be applied to any other body parts to monitor body part alignment and size information via motion and/or position sensors 902 and processing of sensed information relative to at least two sensors 902. In other words, data form two sensors is processed to determent limb alignments and size.

Figure 13:
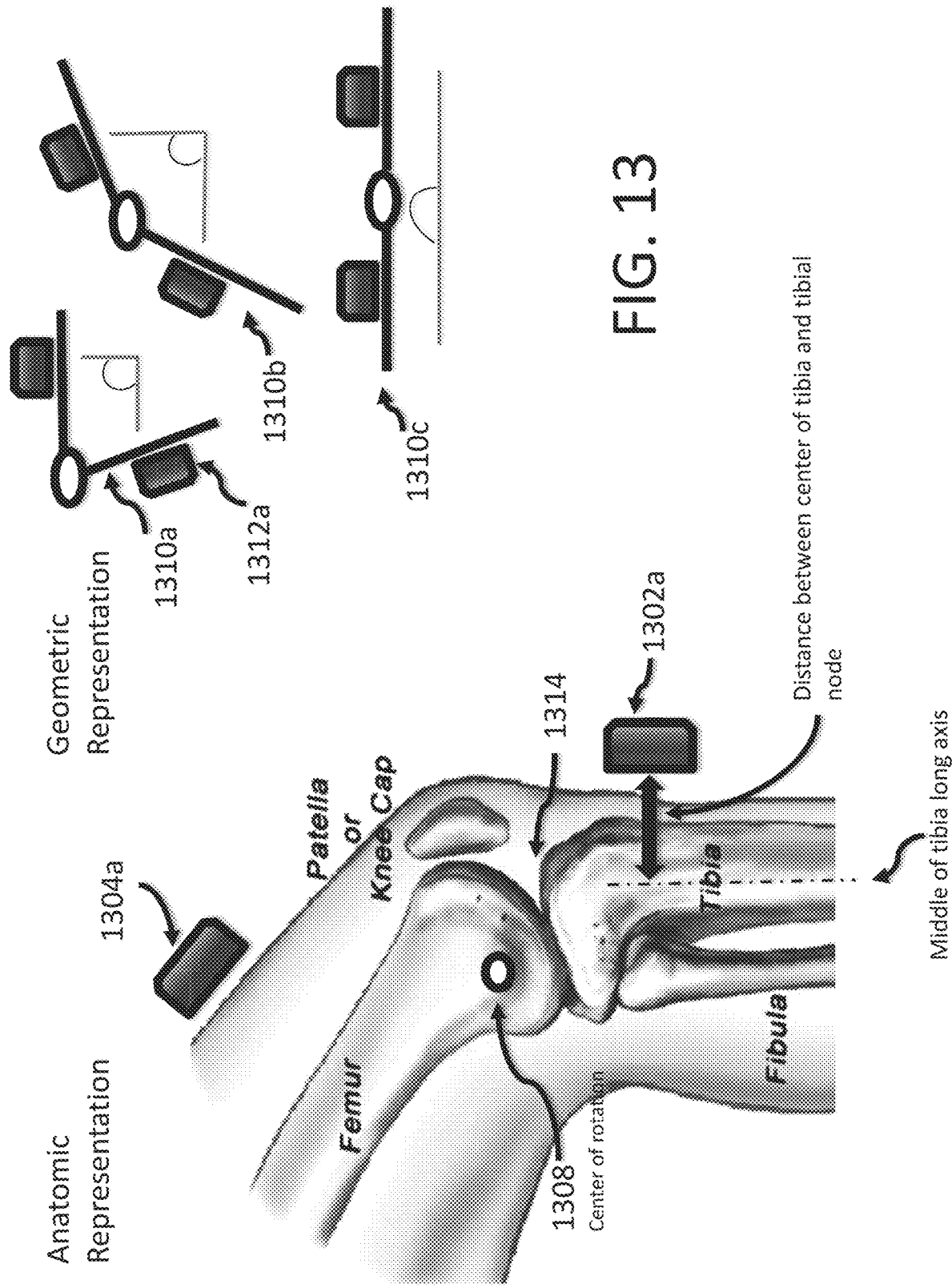
FIG. 13 shows an exemplary depiction of the geometric relation and calculation of a joint's range of motion and relative position of limbs, according to one aspect of the present disclosure.

FIG. 13 shows an exemplary depiction of geometric relation and calculation of joint's range of motion and relative position of limbs.

By knowing the location of the center of the tibia 1306 and the center of rotation of the femur 1308, tibial node 1302 (shown as tibial nodes 1302*a-b* in FIG. 13) and femoral node 1304 (shown as femoral nodes 1304*a-b* in FIG. 13) can be positioned such that an accurate angle of rotation and range of motion of knee joint 1314 may be determined as depicted by geometric drawings 1310 (shown as geometric drawings 1310*a-c* in FIG. 13) showing the relationship between various joint angles and nodes 1312 (labeled only as node 1312*a* in FIG. 13, for clarity).

Moreover, sensor information associated with uninjured limbs can be used as reference to compare with an injured limb to track progress or prescribe therapy. The following is an example of comparing objective data from injured limb against uninjured limb:

1: Single Leg hop: same as uninjured limb +4; 85% uninjured: +2; 84-70%: 0; <70%: −3); test protocol: to calculate distance "press start" for device; starting position for this maneuver is a semi-crouched position on the single limb being tested; initiate hop by swinging arms forward, simultaneously extending at the hip and knee, and hoping forward as far as possible while being able to land safely on the same limb and hold it for 1 sec, repeat this 3 times on each leg. (See, G Meyer: Utilization of Modified NFL Combine Testing to Identify Functional Deficits in Athletes Following ACL Reconstruction. J Orthopedic& Sport Physical Therapy 41(6)2011 p. 377)

2: TRIPLE HOP. Same protocol as before but 3 consecutive hops on same leg with a controlled landing at end. Measure total distance covered and compare side to side.

3: Core Assessment: Combined amount of "sway" or micro agitation in nodes during planking testing. Will need to conduct some testing to set parameters. Straight face down on elbows hand lightly touching each other, measure time plus sway.

4: Speed or gait: Measure stride length and asymmetry. Normal symmetric walking: +3; 99-85%: 1; <85%: −2. Running-nml pattern and symmetric: +5; 99-85%: +3; 84-70%: 0; <70%: −3. Calculate stride length and the timing b/w feet.

5: Single leg balance: Comparing legs at 30 Flexion at knee, looking for sway side to side, front to back as well as more micro-scopic oscillations of node—as a proxy for strength. Develop scoring cut offs via test based on combination of time and disturbance from a baseline.

Equilibrium of a body joint is another important parameter for calculating a users injury risk index upon resuming unrestricted activities. Equilibrium of a joint is defined by the relative stability of that joint, which can be determined by muscle strength (such as the muscles capability of resistance to fatigue or endurance). For example, wobbling or quivering of a joint are examples of muscle fatigue during an activity, which indicate lower muscle strength and therefore a lower equilibrium. Proprioception is the sense of the relative position of neighboring parts of the body and strength of effort being employed in movement, and the ability to sense stimuli arising within the body regarding position, motion, and equilibrium. For example, if a person is blindfolded, that person will know through proprioception if their arm is above their head or hanging by the side of their body. The system of the present disclosure will track (for example during a users post-surgery rehabilitation program) the equilibrium and relative stability of a joint using the data collected from the sensor devices, which will show improved proprioception.

BaziScore

BaziScore is a number, which the system of the present disclosure calculates based on an algorithm to index an individual's risk of injury to a joint at any given time. A higher score indicates a reduced injury risk and a higher readiness to resume unrestricted activities by a user, where the highest BaziScore will represent the threshold that a user must reach or pass in order to complete rehabilitation and resume activities with the least risk of injury. In order to calculate the BaziScore, this system uses different sets of data. An objective set of data and a subjective set of data. The objective data is collected using the sensor devices while a patient, e.g., an injured user, performs certain activities assigned by a health care provider. The objective data can also include that collected from healthy persons. These activities can include a single leg hop, a side plank, a single leg balance, a jump from one foot above the ground, or any other various types of activities. Each activity is assigned to a user to perform while wearing the portable sensors of the present disclosure in order to collect alignment, range of motion, and equilibrium data from a set of joints on the body. The system of the present disclosure uses a comparative analysis of the data received from a set of joints (for example the left knee joint and the right knee joint) to assign scores for each parameter considered. For example, a jumping test measuring the range of motion of the knee will provide range of motion data from the right and left knee, one of which has been previously injured and is rehabilitating. Comparing the range of motion of the previously injured knee to the normal knee forms the basis of the scoring system for BaziScore. For example if the range of motion of the rehabilitating knee is the same as the range of motion of the normal knee, a score of positive three (+3) is assigned to range of motion. However, if the range of motion of the rehabilitating knee is within 15 percent of the normal knee, a score of positive one (+1) is assigned and if it is below 15 percent, a score of zero (0) is assigned to range of motion. The same concept is applied to alignment and equilibrium of a joint. The subjective set of data is a collection of user responses to a complex multifactorial questionnaire, which will vary according to each user based on the nature and timing of a user's injury, with assigned scores for all responses available to the user.

The subjective questionnaire will provide measurements of the injured users perceptions and the injured users subjective assessment of how their joint is feeling. The score assigned to each response is based on a user's relative injury risk and readiness to resume unrestricted activities with the least amount of risk from. The subjective data can also include responses from healthy persons. The score can be derived by comparing data between injured users' and healthy peoples' responses. Some examples of questions and answers from a questionnaire including assigned scores in parentheses are as follows: Do you feel unstable while running? Yes (−2/hard stop) No (+4). The furthest I can run without stopping my leg is: ¼ mile (−1) ½ mile (+0) 1 mile (+4) 2 miles (+6) greater than 2 miles (+8). Compared to my uninjured leg, I feel I can jump, sprint, and stop quickly: the same or better (+5) about as well (+2) not very well (−4). On a scale of 0 (no pain) to 10 (worst pain imaginable) rate your pain while walking: 1-3 (+2) 4-7 (0) 7-10 (−3). Certain answers of a question may include a hard stop as well as a score, which means that even though the user receives a score for their answer, regardless of the user's total score based on objective and subjective scores, the user cannot pass the threshold for resuming unrestricted activities with least likelihood of injury risk.

The BaziScore algorithm adds scores collected from the user questionnaire as well as scores calculated based on an analysis of the objective data from the sensors. In addition to these scores, the algorithm includes time restrictions for clearing thresholds, which are entered into the system by the healthcare providers. For example, if a user had a knee surgery, a health care provider or physical therapist enters the date of the surgery for that user as well as timelines from the date of the surgery to pass the BaziScore threshold.

Figure 14:
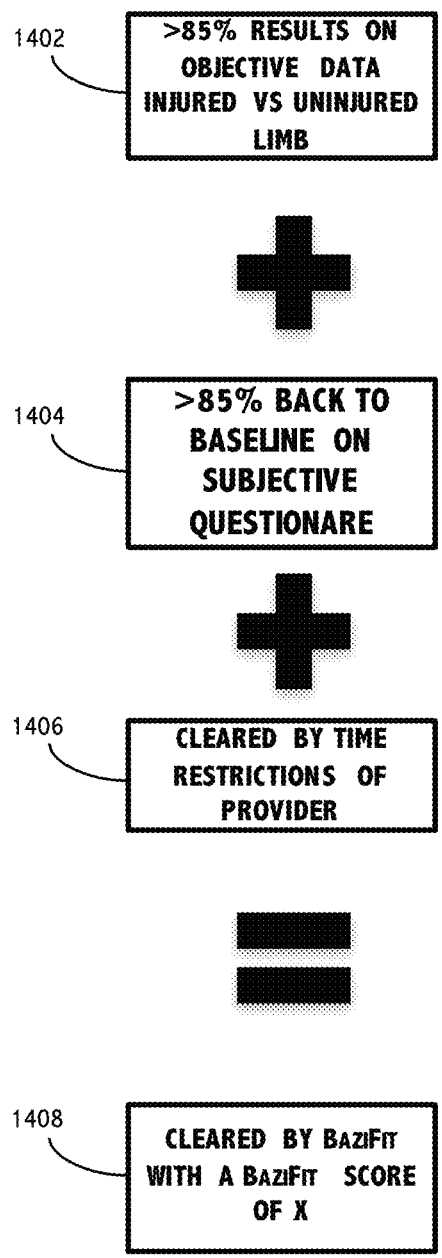
FIG. 14 shows a simple flow chart of a BaziFit Readiness algorithm, according to one aspect of the present disclosure.

FIG. 14 shows a simple flow chart of BaziFit Readiness algorithm:
- 1402) >85% results on objective data injured vs uninjured limb is determined;
- 1404) >85% Back to baseline on SUBJECTIVE questionnaire; and
- 1406) Cleared by time restriction of provider;
- 1408) Results in clearance by BaziFit by a score.

The system allows questions to be asked and answered at various times in rehab. Below are examples of subjective questionnaire. All questions can have a n/a option, hard stop means can't pass but will still get a score:
Do you feel unstable with Walking: Yes: hard stop and −5; No: cont. and +1
Do you feel unstable with Running: Yes: hard stop and −2; No: cont. and +4
Does your leg ever feel unsteady during aggressive activities (jumping, twisting, squatting, dancing, attempting sports: No: +4; Rarely: +1; Frequently: hard stop and −2
Compared to my uninjured knee during squats and leg extensions I can lift: The same or more weight: +3; about 85%: +1; <85%: −2
Answer the following 3 questions on a scale from 0=no pain to 10=worst pain imaginable:
Pain with walking: 0-3: +2; 4-7: 0; >7: −3
Pain with climbing stairs: 0-3: +3; 4-7: +1; >7: −2
Pain with running: 0-3: +4; 4-7: +2; >7: 0
When I run my legs feel the same: Yes: +3; No: 0
The furthest I can run without stopping because of my leg is: ¼ mile: −1; ½ mi: +0; 1 mi: +4; +2 mi: +6; >2 mi: +8
I feel I can run and walk without problems/concerns or fear: Yes: +3; No: −2
Compared to my uninjured leg, I feel I can jump, sprint, and stop quickly: the same or better: +5; about as well: +2; not very well: −4
When I practice the same sport in which I was injured I feel: Nervous: −2; Okay and fit: +2; as good as before the injury: +5
During all of my rehab, fitness and recreational activities my injured leg feels: tired and weak: −3; a little different than my other: +1; as good or better: +4

The present disclosure can be used to provide assessment for cleared-by-time restrictions of health provider. The requirements would be date of surgery, date earliest surgeon clears patient to run and jump (generally fixed at time of surgery—based on procedures type of graft); surgeons post-op rehab protocol or referral to physical therapist based by meeting subjective/objective criteria (assessed in office or rely on PT assessment). Patient or therapist or surgeon will have to enter this information.

By repetition, the system builds its database and gets points used to logging into a website portal with an incentive program to generate views and traffic. The system can be used to manage and plan treatment and therapy, for example are 2/4/6/8/10/12/18/24 months post-operation. The system can be a platform for doctors, therapists, fitness professionals, and organizations to administer their own questionnaire through the SaaS. Various scoring arrangements can be developed as more data is captured.

Figure 15:
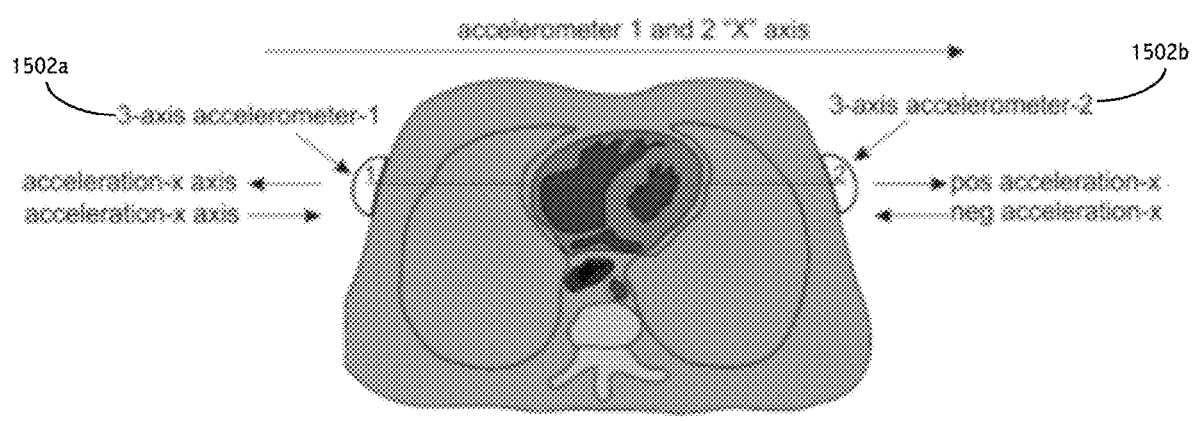
FIG. 15 shows the system of the present disclosure being implemented for heartbeat detection, according to one aspect of the present disclosure.

FIG. 15 shows the system of the present disclosure being implemented for heartbeat detection using one or more pairs of 3-axis accelerometers 1502 (shown as 3-axis accelerometers 1502a-b in FIG. 15) or 3-axis gyroscopes. The heartbeat detection may be suitable for measurement during physical exercise/activity. Heartbeat detection is achieved by differentiating the signals obtained from two accelerometers/gyroscopes 1502 placed on the both/opposite side of the chest in line—across the heart with aligned axis as shown in FIG. 15. The signals caused by subject movement (running, jumping etc.) will be similar and their differentiation/subtraction will give a minimal result (ideally zero). Since the ideal alignment is almost impossible to achieve, then alignment compensation should be done in the analysis software by using digital signal processing.

Figure 16:
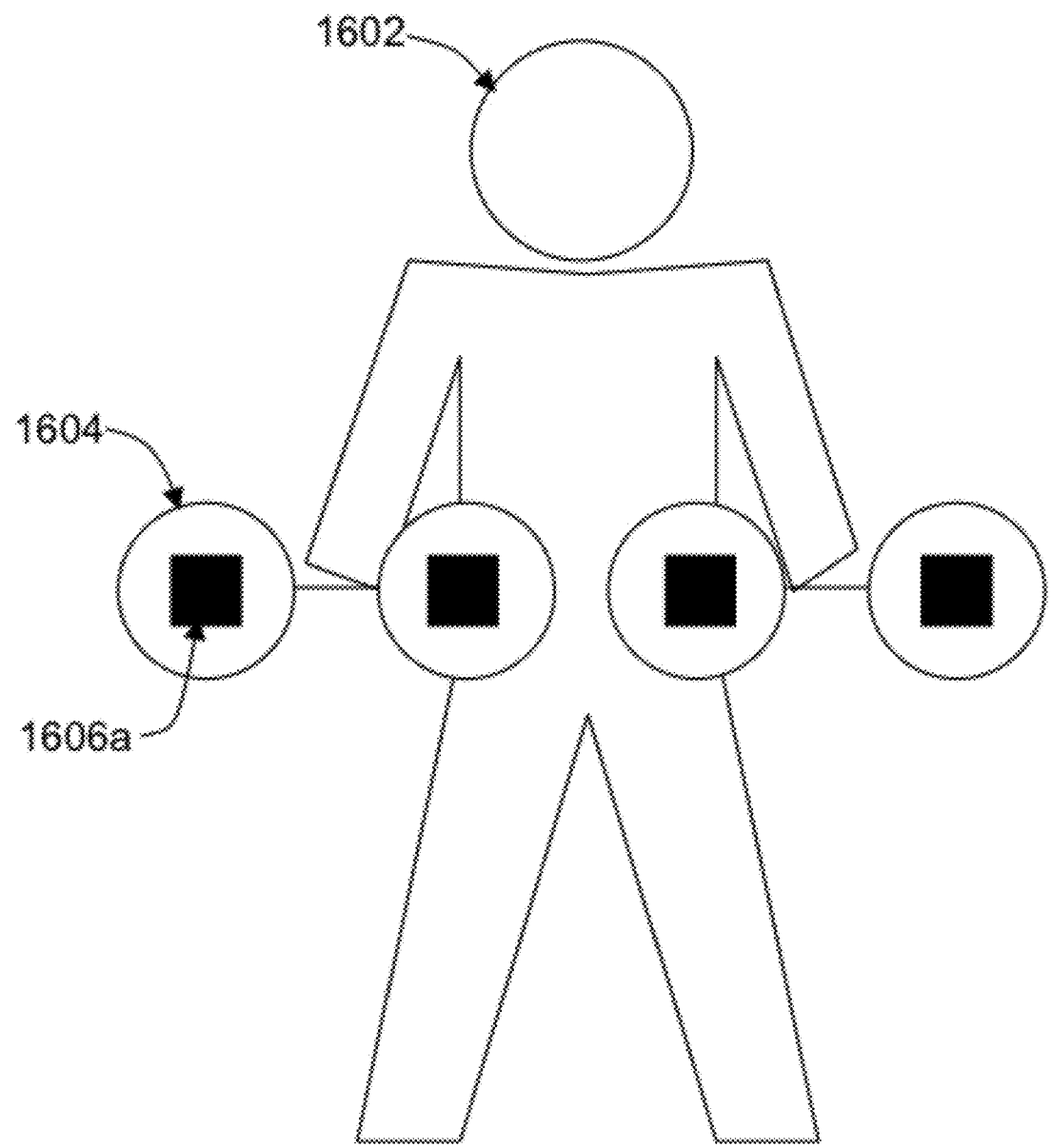
FIG. 16 is an image of a user utilizing an exemplary activity device integrated with a plurality of sensors, according to one aspect of the present disclosure.

Referring now to FIG. 16, an image of a user 1602 utilizing an exemplary activity device 1604 integrated with a plurality of sensors 1606 (labeled only as sensor 1606a in FIG. 16, for clarity), according to an aspect of the present disclosure, is shown.

In some aspects, sensors 1606 are not worn on the body of user 1602, but rather may be integrated with one or more external objects such as activity device 1604, such as the dumbbells shown in FIG. 16. Sensors 1606 may comprise brain nodes 904 as well as sensor devices 902. In some embodiments, sensors 1606 only comprise brain nodes 904. In some additional embodiments, every sensor comprises at least one computer processor or CPU. Sensors 1606 may be permanently or removably attached to or integrated with activity devices 1604. By way of example and not limitation, a base or attachment connector 2708 (not shown in FIG. 16) may be permanently or removably integrated with an activity device 1604 and sensors 1606 may be removably attachable to the base or attachment connector 2708. Sensors 1606 may be removably or permanently attached to the base or attachment connector 2708, or directly to activity device 1604 by being snapped on or screwed on, or by being attached via one or more fastening elements, including but not limited to screws, bolts, nuts, clips, clamps, clasps, rivets, magnets, cable ties, adhesives, hook-and-loop fasteners, or any other similar element(s) as may be apparent to those skilled in the relevant art(s) after reading the description herein.

Sensors 1606 integrated with an external object such as activity device 1604 may be configured to sense various aspects of the motion of activity device 1604 as it is utilized by user 1602. By way of example and not limitation, sensors 1606 may utilize one or more accelerometers, gyroscopes, magnetometers, capacitive, ultrasonic, current, hall effect, inductive, Doppler, laser, transformer, displacement transducer, photodiode, piezo-electric, potentiometer, proximity, rotary, and/or similar components as may be apparent to those skilled in the relevant art(s) after reading the description herein in order to detect the vibration, position, location, stability, speed, and/or any similar aspects of activity device 1604 while in motion, and send the detected information to one or more user computing device(s) 1706 (not shown in FIG. 16), thereby allowing one or more software applications associated with user computing device 1706 to perform analytical functions to calculate various fitness measurements and/or scores related to user 1602, including but not limited to the neuromuscular efficiency, strength, stability, and/or calories burned by user 1602 as measured during a given period of movement, as well as any similar fitness measurements as may be apparent to those skilled in the relevant art(s) after reading the description herein. Additionally, the one or more software applications associated with user computing device 1706 may be used to determine a likelihood of injury for user 1602, as well as to track the rehabilitation progress of user 1602 after an injury. In some aspects, subjective data may be input into user computing device 1706 in conjunction with the objective data provided by sensors 1606 in order to assist the one or more software applications provide a more accurate analysis to user 1602.

User 1602 may be any person who uses sensors 1606 to track at least one physical movement. In some aspects, user 1602 could be an animal, such as a pet. Health professionals may also be users 1602, in some additional aspects.

User computing device 1706 may comprise any device comprising at least one computer processor, at least one display screen, and at least one input device and being capable of running the one or more software applications of the present disclosure and receiving information from and/or sending information to sensors 1606 and/or various computational databases, including but not limited to desktop computers, laptop computers, notebook computers, tablet computers, personal digital assistants (PDAs), mobile telephones, smart telephones, gaming consoles, and the like. The at least one input device may comprise a keyboard, mouse, joystick, touchscreen, graphical user interface, or any other similar input device as may be apparent to those skilled in the relevant art(s) after reading the description herein.

The one or more software applications of the present disclosure may be downloaded to user computing device 1706, operated by user computing device 1706 without being downloaded, or accessed and used by user computing device 1706 via one or more websites, or via any other means as may be apparent to those skilled in the relevant art(s) after reading the description herein. Such application(s) may be configured to work with one or more application servers to perform one or more storage, analytical, presenting, retrieval, determining, and/or caparison functions while communication with user computing device 1706 and/or sensor(s) 1606. In some aspects, the application(s) may be configured to perform these and other functions without an application server.

Types of activity devices 1604 that may be integrated with one or more sensor(s) 1606 may include but are not limited to dumbbells, barbells, suspension training equipment (such as TRX® cables available from Fitness Anywhere LLC of San Francisco, Calif.), BOSU® balance trainers (available from Hedstrom Fitness of Ashland, Ohio), resistance bands, surfboards, balance boards, skateboards, snowboards, water skis, snow skis, and any other appropriate pieces of sporting and/or exercise equipment as may be apparent to those skilled in the relevant art(s) after reading the description herein.

When suspension training cables are used as activity device 1604, for example, one or more sensor(s) 1606 may be incorporated therewith to, among other things, detect vibrations in the cables during use. If, while user 1602 is pulling on the cables, there is a significant amount of vibration within the cables, sensor(s) 1606 will detect this and the one or more software applications associated with user computing device 1706 will indicate a relatively low strength level for the muscles of user 1602 targeted by that exercise and communicate such information to user 1602 via one or more display screens associated with user computing device 1706.

Similarly, while user 1602 is using one or more dumbbells, such as the ones shown in FIG. 16, sensors 1606 will be particularly sensitive to detecting the stability of the dumbbells, Fluid motions on the part of user 1602 would indicate high stability and strength for the muscles being used, while a lot of vibration and gyration would indicate instability and likely muscle weakness.

Regardless of what type of activity device 1604 is used, sensors and/or the one or more software applications associated with user computing device 1706 are helpful for providing continuous feedback to user 1602 during an exercise or activity so that user 1602 can make form, resistance amount, and other changes as necessary in order to make faster improvements, which may be especially useful while rehabilitating an injury.

Figure 17:
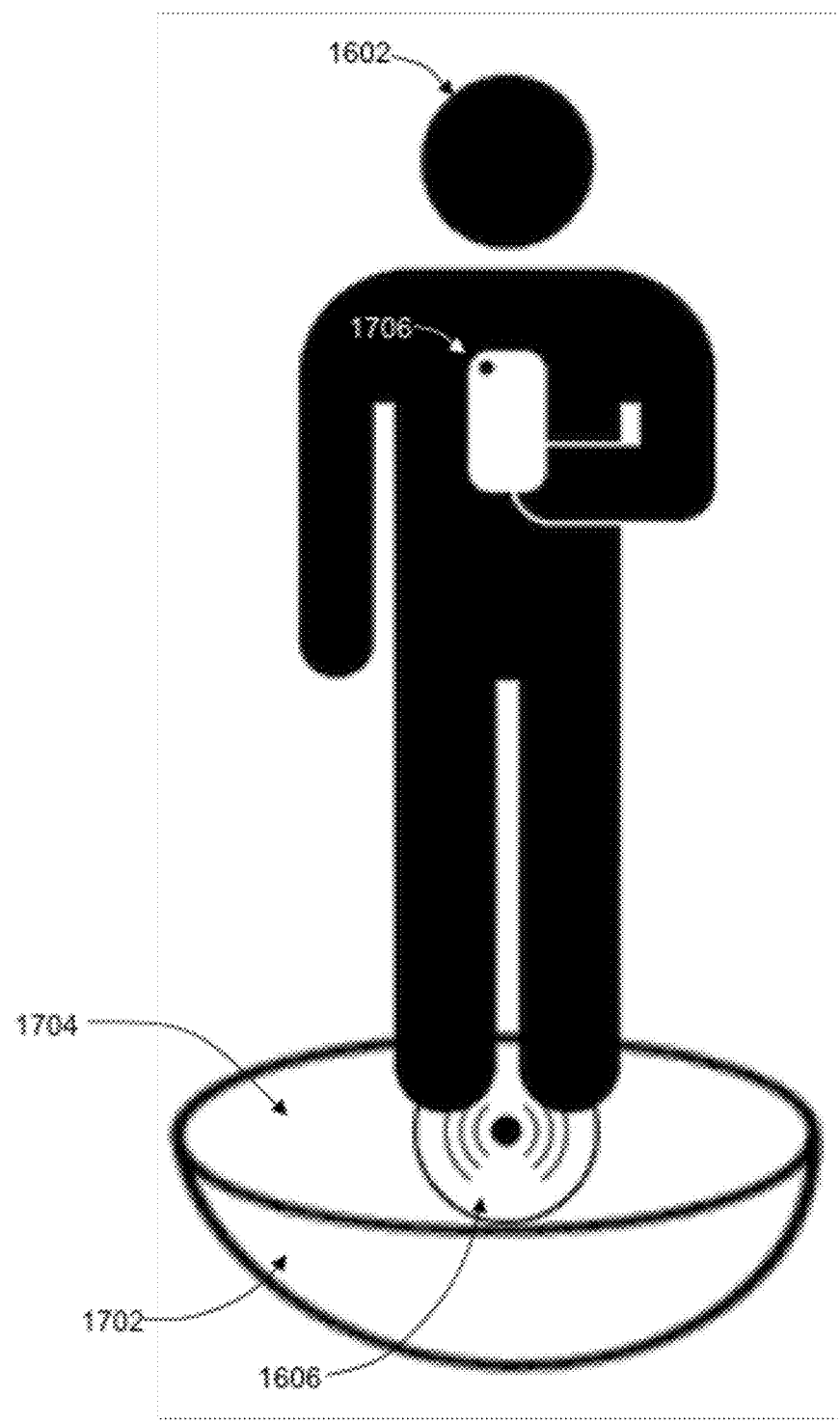
FIG. 17 is an image of a user utilizing a second exemplary activity device integrated with a sensor, according to one aspect of the present disclosure.

Referring now to FIG. 17, an image of a user 1602 utilizing a balance trainer 1702 integrated with a sensor 1606, according to an aspect of the present disclosure, is shown.

In some aspects, user 1602 may utilize a sensor 1606 integrated with a balance trainer 1702, such as a BOSU® balance trainer (available from Hedstrom Fitness of Ashland, Ohio). In some aspects, sensor 1606 may be integrated with a substantially flat top surface 1704 of balance trainer 1702. Sensor 1606 may be communicatively coupled with user computing device 1706, thereby allowing use 1602 to instantly view feedback regarding the performance of user 1602 upon balance trainer 1702.

While on balance trainer 1702, user 1602 may engage in a variety of movements that may cause balance trainer 1702 to vibrate, tilt, rotate, oscillate, raise, or lower. All of these motions of balance trainer 1702 may be detected by sensors 1606 communicating with one or more software applications associated with user computing device 1706, which may then use the received information to calculate and/or present various fitness/health elements for/to user 1602, including but not limited to neuromuscular efficiency, strength, stability, and calories burned.

By way of example and not limitation, if, while user 1602 is using balance trainer 1702, sensor 1606 detects a lot of vibration being experienced by balance trainer 1702, this would cause the software application(s) associated with user computing device 1706 to determine that the stabilizer muscles being used are relatively weak. User computing device 1706 would then provide that feedback information to user 1602 via one or more display screens.

Figure 18:
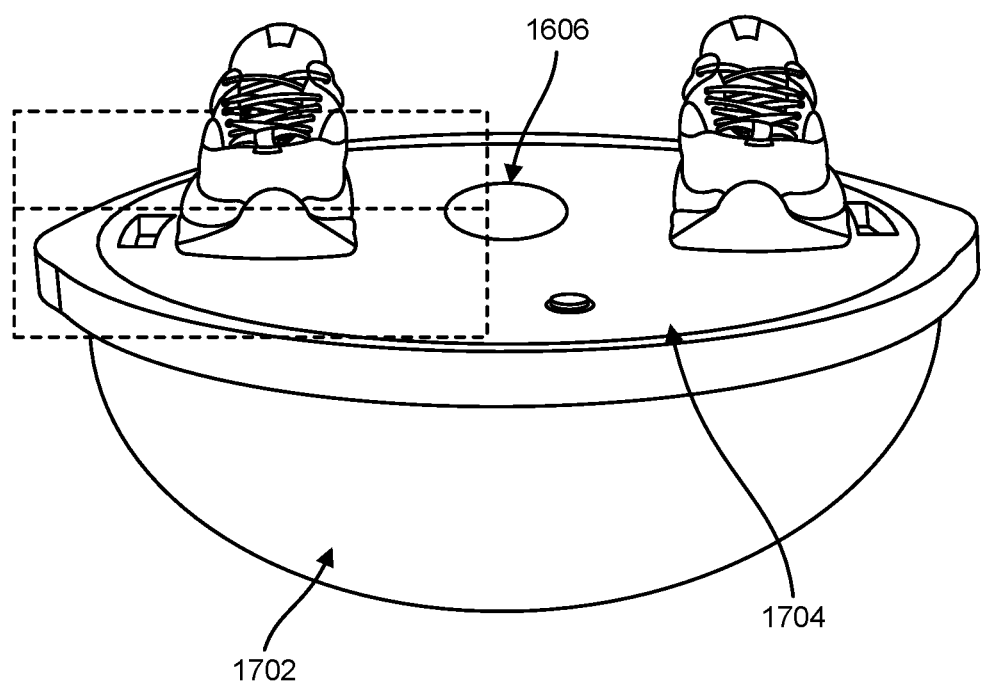
FIG. 18 is a perspective view of an exemplary activity device integrated with a sensor, according to one aspect of the present disclosure.

Referring now to FIG. 18, a perspective view of an exemplary balance trainer 1702 integrated with a sensor 1606, according to an aspect of the present disclosure, is shown.

In some aspects, sensor 1606 may be located upon a relatively central portion of circular top surface 1704 of balance trainer 1702. Sensor 1606 may be configured such that is comprises a top, dome-like surface that protrudes upwardly when securely fastened upon balance trainer 1702. Sensor 1606 may comprise an outer surface made of rigid, durable materials including, but not limited to, metals, plastics, other polymers, and any other appropriate material(s) as may be apparent to those skilled in the relative art(s) after reading the description herein.

In some aspects, sensor 1606 may be securely fastened directly to surface 1704 of balance trainer 1702. In some additional aspects, a base or surface attachment 2708 (not shown in FIG. 18) may be permanently or removably attached to/integrated with surface 1704 and then sensor 1606 may snap, twist, or otherwise adhere to the base and/or surface attachment 2708 as described previously.

Figure 19:
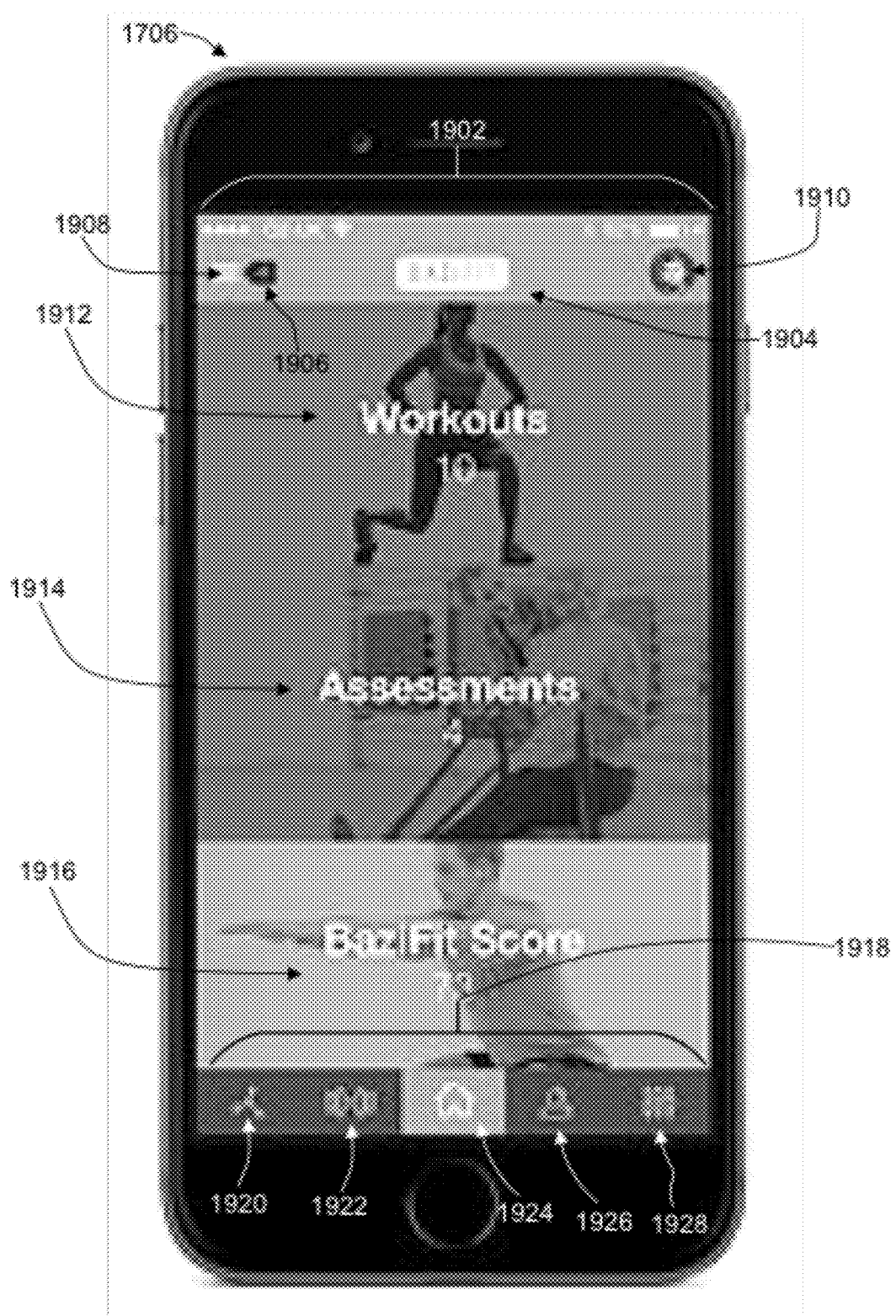
FIG. 19 is an image of an exemplary application home screen displayed upon a graphical user interface of an exemplary user computing device, according to one aspect of the present disclosure.

Referring now to FIG. 19, an image of an exemplary home screen displayed upon a graphical user interface of an exemplary user computing device 1706, according to an aspect of the present disclosure, is shown.

In aspects wherein user computing device 1706 comprises a graphical user interface with touchscreen capabilities, the home screen provided by the one or more software applications associated with user computing device 1706 may, in some aspects, resemble that shown in FIG. 19. In such aspects, the home screen may comprise top bar 1902, screen identifier 1904 (in the case of the home screen, the screen identifier 1904 may display "BAZIFIT"), back arrow 1906 which allows user 1602 to return to the previous page, menu button 1908 which allows user 1602 to view a menu for the software application thereby displaying a variety of options, user 1602 photograph or image 1910 (which may, among other things, serve as a link to a user profile), a link 1912 to the workouts section of the software application (along with a numerical representation of the number of workouts available and/or completed), a link 1914 to the assessments section of the software application (along with a numerical representation of the number of assessments available and/or completed), and a link 1916 to the BaziFit score section of the software application (along with the current and/or most recent BaziFit score for user 1602), and lower menu bar 1918, which comprises a tab for the assessments section 1920, a tab for the workouts section 1922, a tab for the home screen 1924, a contacts tab 1926 to connect with/message/chat with/or otherwise engage with other users 1602 via one or more social networking platforms, and a BaziFit score section tab 1928. Being that the home screen is currently displayed, tab 1924 for the home screen is currently illuminated.

Figure 20:
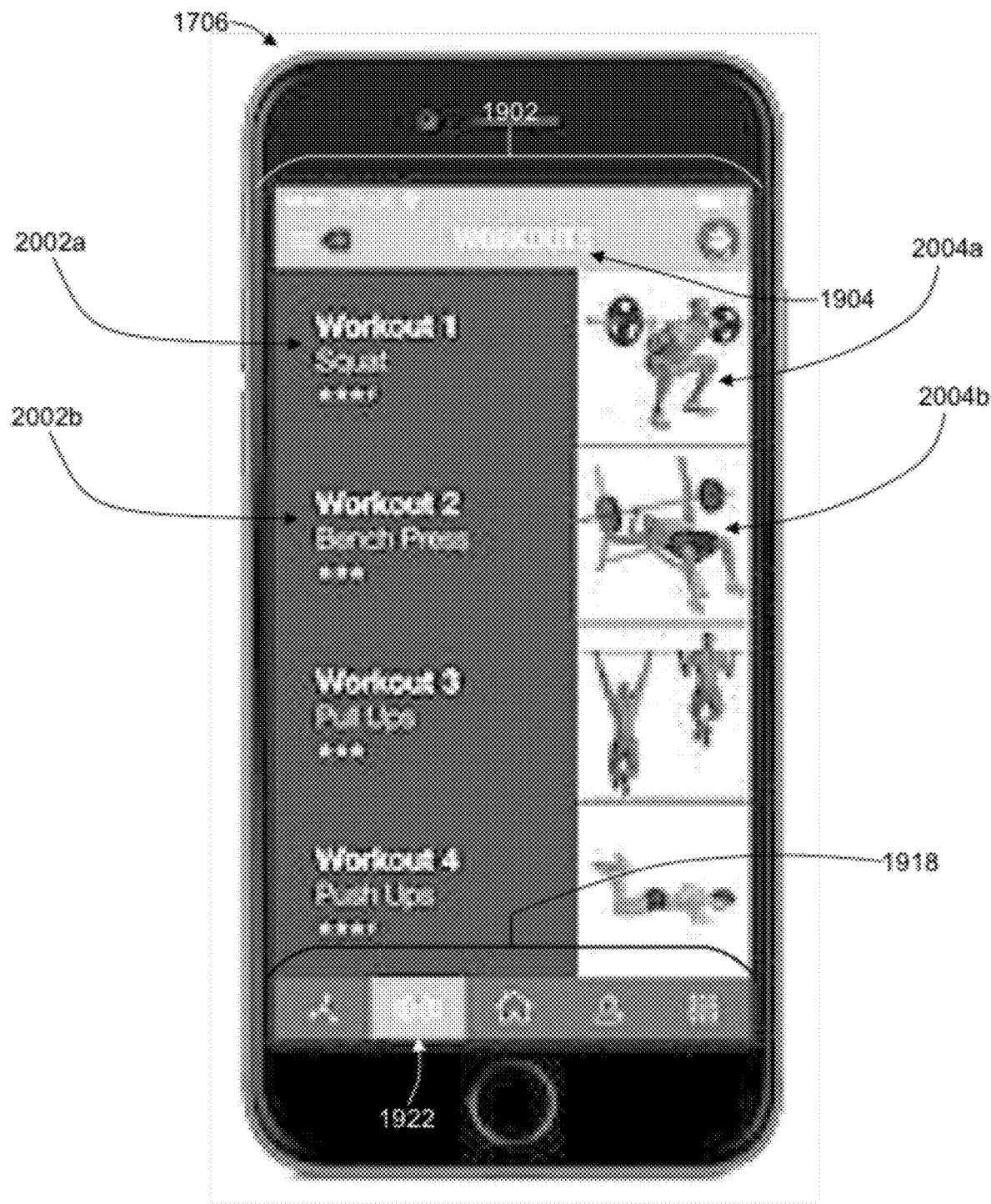
FIG. 20 is an image of an exemplary application workouts section screen displayed upon a graphical user interface of an exemplary user computing device, according to one aspect of the present disclosure.

Referring now to FIG. 20, an image of an exemplary workouts section screen displayed upon a graphical user interface of an exemplary user computing device 1706, according to an aspect of the present disclosure, is shown.

In aspects wherein user computing device 1706 comprises a graphical user interface with touchscreen capabilities, the workouts section screen provided by the one or more software applications associated with user computing device 1706 may, in some aspects, resemble that shown in FIG. 20 with "workouts" displayed as screen identifier 1904. In such aspects, the workouts section screen may comprise, in addition to the top and bottom elements described with regard to FIG. 19, workout information 2002 (labeled only as workout information 2002*a-b* in FIG. 20, for clarity). Workout information 2002 may, in some aspects, comprise a workout name, a workout number, and a workout rating. The workout rating may, for example, be representative of how well user 1602 performed the workout (as determined either by user 1602, by the one or more software applications associated with user computing device 1706, or by a third party observer), how user 1602 rated the workout, or how other users 1602 have rated the workout.

In addition to workout information 2002, the workouts section screen may comprise at least one picture 2004 (labeled only as pictures 2004*a-b* in FIG. 20, for clarity) for each workout to give user 1602 a general idea of what it entails.

Selecting a given workout may cause that workout session to be displayed upon user computing device 1706 or upon any visual display device communicatively connected to user computing device 1706 and/or the one or more software applications associated therewith. While user 1602 is being presented with the workout content, and user 1602 engages in the workout, user 1602 may also receive real-time and/or post-workout performance feedback, thereby engaging in a virtual personal training session with two-way communication. In some aspects, such feedback is stored and viewed later by user 1602. The feedback may comprise audio and/or visual elements. The feedback may comprise automated responses triggered by how well the one or more software applications associated with user computing device 1706 and sensor(s) 1606 determine user 1602 to be doing; or, in some aspects, a remote human observer may provide live and/or recorded feedback, such as, by way of example and not limitation, by using one or more webcams, microphones, and/or speakers. Feedback and two-way communication capabilities for other scenarios beyond workout sessions, including but not limited to rehabilitation sessions, physical therapy sessions, lessons (for instance, by way of example and not limitation, how to play a musical instrument), as well as any other similar sessions or scenarios as may be apparent to those skilled in the relevant art(s) after reading the description herein.

The workout content may be presented in the form of audio and/or video upon user computing device 1706 and/or upon any appropriate device communicatively connected therewith as may be apparent to those skilled in the relevant art(s) after reading the description herein, including but not limited to television sets, smartphones, tablet computers, notebook computers, laptop computers, desktop computers, and the like. Additionally, in some aspects, user 1602 may be instructed to initiate a certain workout session on user computing device 1706 in order to take part in a live in-person exercise class or similar event in order to receive performance feedback that may be accessed either in real-time or after the workout session has ended. In some additional aspects, workout content of any type is provided by one or more third parties.

Figure 21:
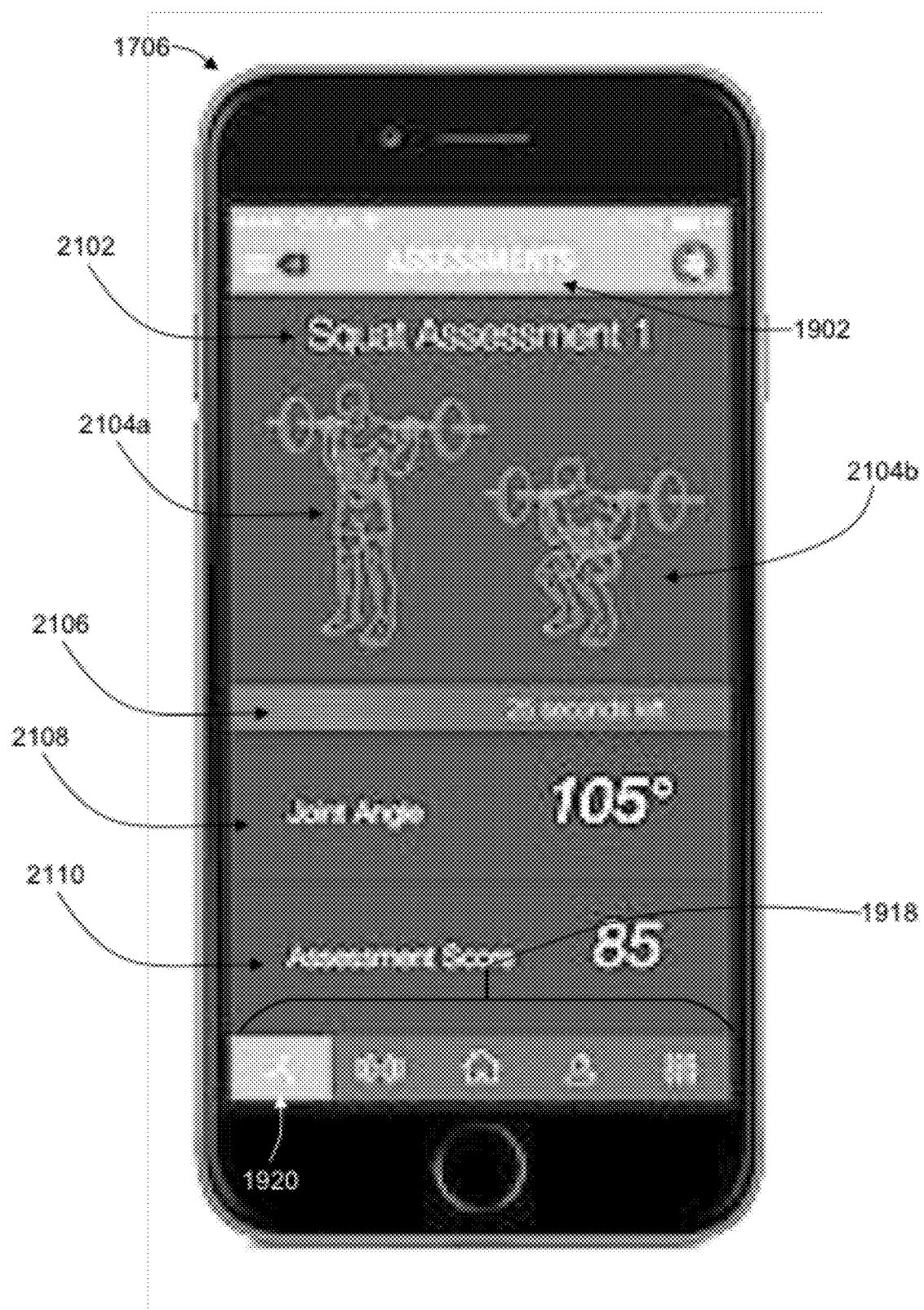
FIG. 21 is an image of an exemplary application assessments section screen displayed upon a graphical user interface of an exemplary user computing device, according to one aspect of the present disclosure.

Referring now to FIG. 21, an image of an exemplary assessments section screen displayed upon a graphical user interface of an exemplary user computing device 1706, according to an aspect of the present disclosure, is shown.

In aspects wherein user computing device 1706 comprises a graphical user interface with touchscreen capabilities, the assessments section screen provided by the one or more software applications associated with user computing device 1706 may, in some aspects, resemble that shown in FIG. 21 with "assessments" displayed as screen identifier 1904. In such aspects, the assessments section screen may comprise, in addition to the top and bottom elements described with regard to FIG. 19, an assessment name 2102, pictures of the exercise/move being assessed 2104 (shown as pictures 2104*a-b* in FIG. 21), a time remaining indicator 2106 for the amount of time left in the current exercise session, assessment information 2108 (such as, by way of example and not limitation, a joint angle measurement), and an assessment score 2110. In some aspects, assessment score 2110 may represent a likelihood of injury, rehabilitation progress, readiness, a performance ranking, or similar information for user 1602.

In some aspects, one or more output components integrated with sensor 1606 may work in conjunction with the assessments section screen. By way of example and not limitation, an output component may comprise a visual and/or audio output component, such as a light source, speaker, or the like. Examples of light sources may include incandescent lightbulbs, fluorescent lightbulbs, light emitting diodes (LEDs), as well as any similar light sources as may be apparent to those skilled in the relevant art(s) after reading the description herein. In some embodiments, the light source may be configured to emit at least two different wavelengths of visible light, one for indicating when user 1602 is performing well and another for when user 1602 is not performing well. In some additional aspects, higher light intensities may indicate greater extremes of success or struggling on the part of user 1602. By way of example and not limitation, if a green light indicates that user 1602 is doing well and a red light indicates that user 1602 is not doing well, then a more intense green light would indicate that user 1602 is doing extremely well and a more intense red light would indicate that user 1602 may want to consider stopping the current exercise or activity. An analogous situation could be set up for audio signals, with a high tone indicating that user 1602 is doing well and a lower tone indicating that user 1602 is doing poorly, with louder tones indicating greater extremes. The instantaneous feedback provided by the output component(s) may help user 1602 determine when to stop an exercise or activity, when to increase or decrease resistance (use heavier or lighter weights, use bands with more or less resistance, etc.), or make similar decisions and/or assessments. In some additional aspects, the feedback provided by sensor(s) 1606 to user 1602 makes user computing device 1706 unnecessary. In still some additional aspects, sensor 1606 comprises its own display screen and/or touch screen to, among other things, allow user 1602 to interact with sensor 1606 and/or the one or more software applications without user computing device 1706.

Figure 22:
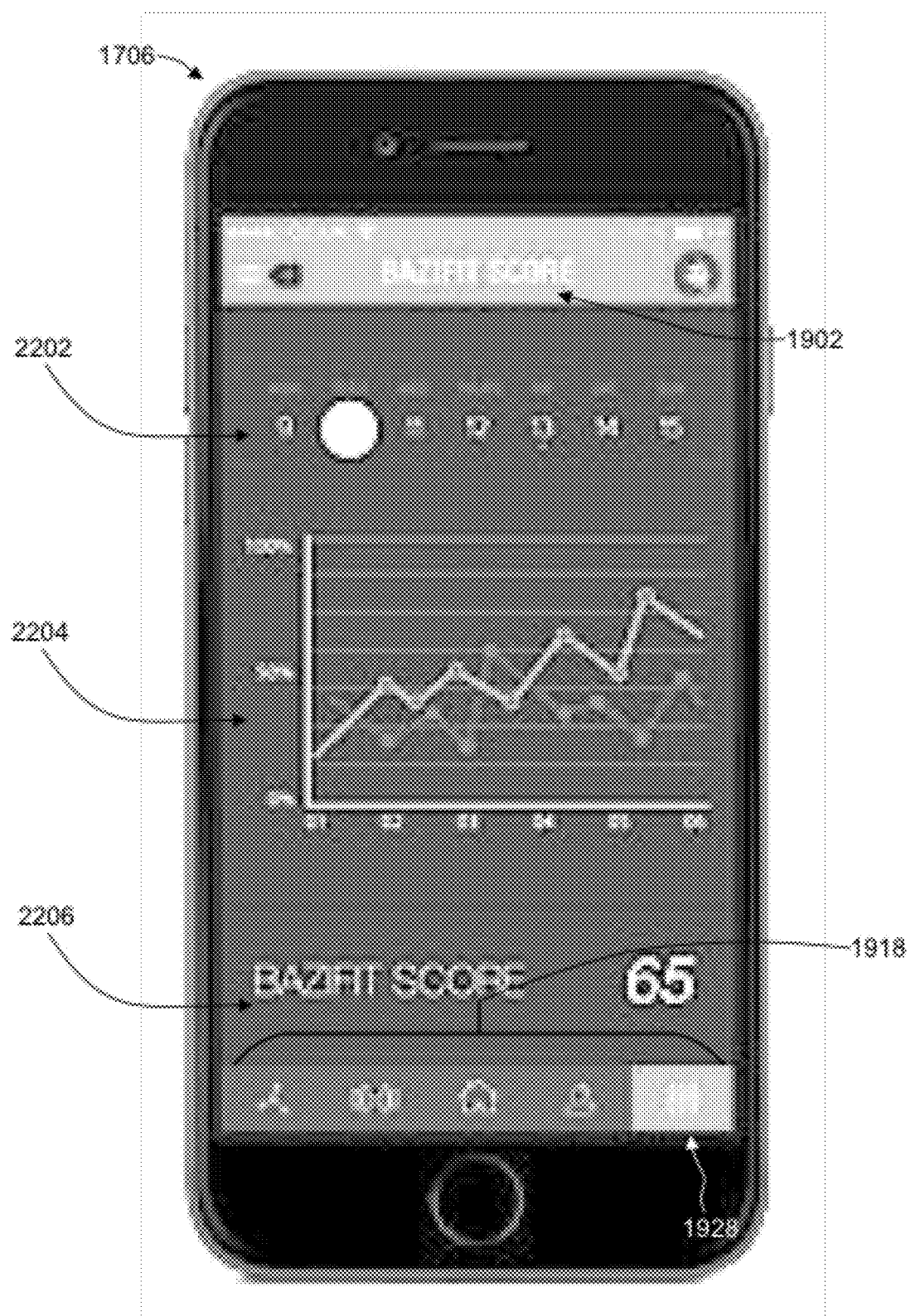
FIG. 22 is an image of an exemplary application BaziFit score screen displayed upon a graphical user interface of an exemplary user computing device, according to one aspect of the present disclosure.

Referring now to FIG. 22, an image of an exemplary BaziFit score section screen displayed upon a graphical user interface of an exemplary user computing device 1706, according to an aspect of the present disclosure, is shown.

In aspects wherein user computing device 1706 comprises a graphical user interface with touchscreen capabilities, the BaziFit score section screen provided by the one or more software applications associated with user computing device 1706 may, in some aspects, resemble that shown in FIG. 22 with "BaziFit score" displayed as screen identifier 1904. In such aspects, the BaziFit score section screen may comprise, in addition to the top and bottom elements described with regard to FIG. 19, a calendar date 2202, at least one performance measuring graph 2204, and a current or previous BaziFit Score 2206. In some aspects, BaziFit score 2206 may represent a likelihood of injury, rehabilitation progress, readiness, a performance ranking (such as neuromuscular efficiency), or similar information for user 1602.

Figure 23:
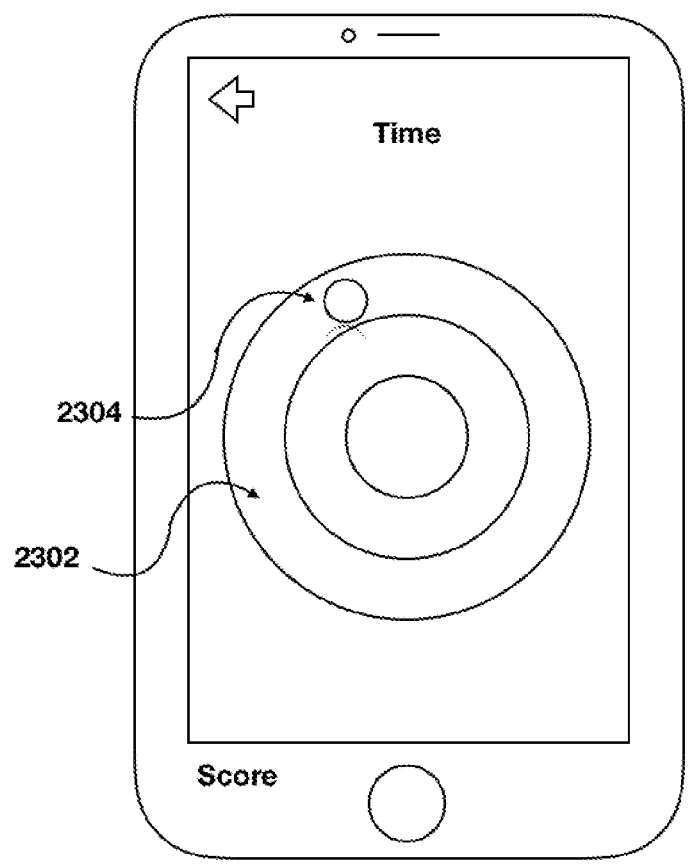
FIG. 23 is an image of an exemplary game utilizing a sensor integrated with an activity device being played upon an exemplary user computing device, according to one aspect of the present disclosure.

Referring now to FIG. 23, an image of an exemplary game utilizing a sensor 1606 integrated with an activity device 1604 being played upon an exemplary user computing device 1706, according to an aspect of the present disclosure, is shown.

In some aspects, one or more sensors 1606 may be integrated with one or more activity devices 1604 in order to play games, some of which may be played utilizing user computing device 1706.

One such game may comprise a sensor 1606 integrated with a balance trainer 1702 (or a balance board or similar device). When the game is initiated, a target 2302 may become visible upon a display screen associated with user computing device 1706. Additionally, a small circle 2304 may become visible upon the display screen. Circle 2304 may move about the display screen of user computing device 1706 as user 1602 maneuvers about top surface 1704 of balance trainer 1702, with a possible objective of the game being to get circle 2304 in the center of target 2302. In some aspects, user 1602 may be able to record game scores, with game scores improving as user 1602 gets circle 2304 to the center of target 2302 faster, with more fluid motions, with overall greater stability, etc., thereby showing increased performance, including increased neuromuscular efficiency.

Figure 24:
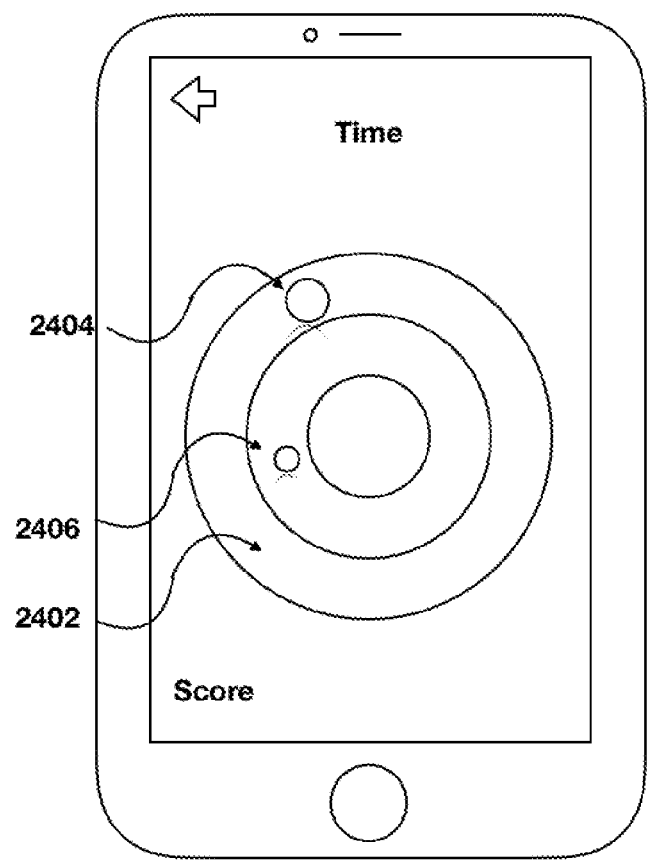
FIG. 24 is an image of a second exemplary game utilizing a sensor integrated with an activity device being played upon an exemplary user computing device, according to one aspect of the present disclosure.

Referring now to FIG. 24, an image of a second exemplary game utilizing a sensor 1606 integrated with an activity device 1604 being played upon an exemplary user computing device 1706, according to an aspect of the present disclosure, is shown.

The game depicted on the display screen of user computing device 1706 in FIG. 24 may be substantially similar to the game depicted on the display screen of user computing device 1706 in FIG. 23, with a substantial difference being that the game depicted in FIG. 24 includes an additional, smaller, circle 2406. In this game, circle 2406 may spontaneously move about the display screen of user computing device 1706 with an objective being that user 1602 has to maneuver about surface 1704 of balance trainer 1702 (or a balance board) in order to get circle 2404 to align with circle 2406. In some aspects, circle 2406 remains stationary until user 1602 aligns circle 2404 with it, while in other aspects circle 2406 only remains in a single location for a brief period of time, and user 1602 must align circle 2404 with it before circle 2406 moves in order to avoid losing or missing out on points. Scores also be calculated for speed, movement fluidity, stability, and overall increased performance, including increased neuromuscular efficiency as described with regard to the game depicted in FIG. 23.

The games depicted in FIGS. 23 and 24 may help increase the neuromuscular efficiency of user 1602. Being on a balance trainer, balance board, or similar device provides a change in the center of gravity for user 1602, thereby putting the neuromuscular activity of user 1602 to the test. Being that the depicted games require significant neuromuscular efficiency to do well, repeated playing of the games will increase the neuromuscular efficiency of user 1602 over time. Tracking game scores is a good way to quantify and track this improvement, as are taking advantage of the assessment scores and BaziFit scores described previously.

Figure 25:
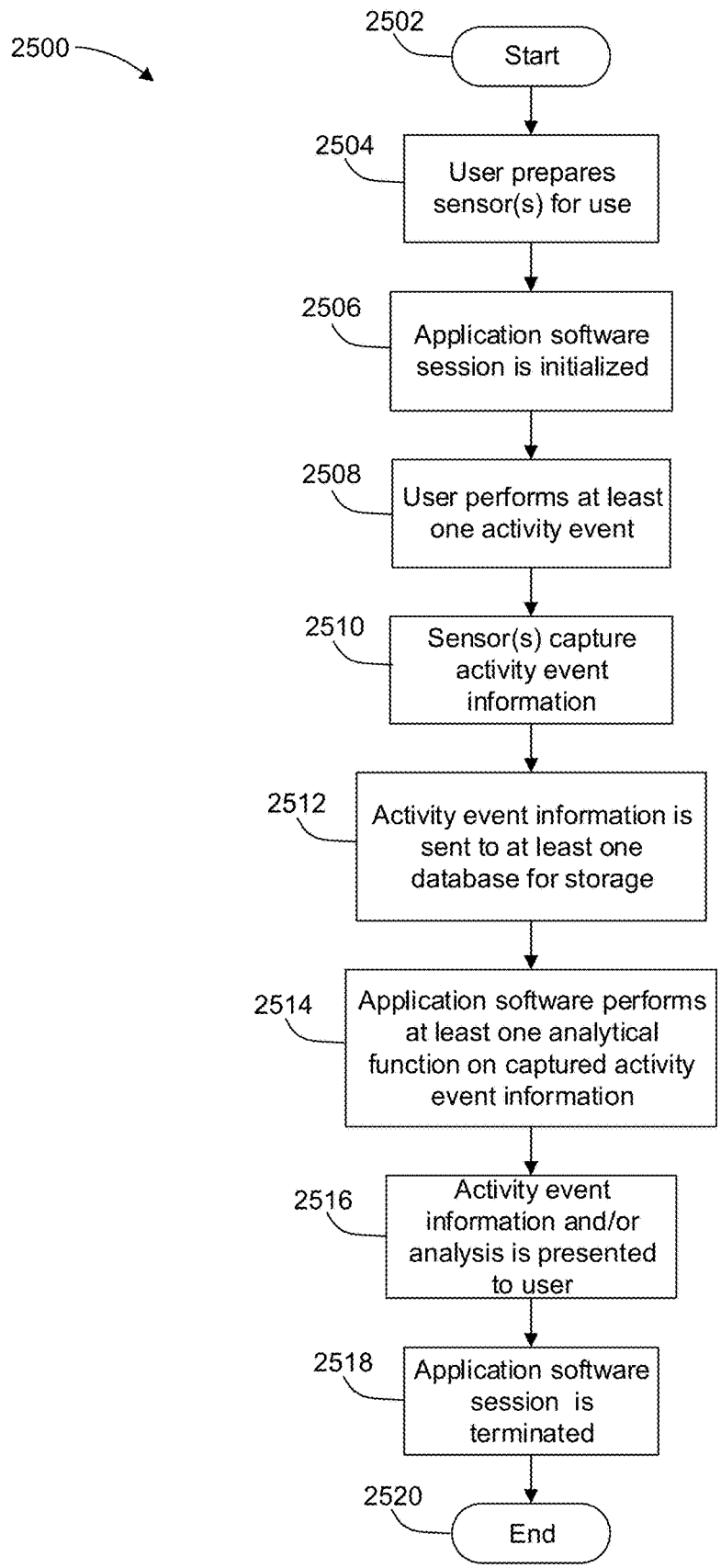
FIG. 25 is a flowchart illustrating an exemplary process for obtaining an evaluation for at least one user activity element, according to one aspect of the present disclosure.

Referring now to FIG. 25, a flowchart illustrating an exemplary process 2500 for obtaining an evaluation for at least one user 1602 activity element, according to an aspect of the present disclosure, is shown.

Process 2500 begins at step 2502 with control passing immediately to step 2504.

At step 2504, user 1602 prepares sensor(s) 1606 for use. This may involve attaching sensor(s) 1606 to the body of user 1602, attaching sensor(s) 1606 to one or more objects, such as one or more activity device(s) 1604, or both. In aspects wherein all of sensor(s) 1606 that are being used function as brain nodes 904, then a minimum of one sensor 1606 may be used; however, when at least one sensor 1606 being used is not a brain node 904, then at least one other sensor 1606 must be used (namely, a brain node 904).

Sensor(s) 1606 attached to the body of user 1602 may be secured using straps, body wraps, arm bands, as well as any other appropriate items as may be apparent to those skilled in the relevant art(s) after reading the description herein. In some aspects, sensor(s) 1606 may be integrated directly with the clothing of user 1602.

Sensor(s) 1606 attached to objects, such as activity devices 1604, may be attached by snapping or twisting sensors 1606 onto a base or attachment connector 2708 (not shown in FIG. 25) integrated with the objects, by snapping or twisting sensors 1606 onto the objects themselves, or by using any of a variety of appropriate fasteners, including but not limited to screws, bolts, nuts, clips, clamps, clasps, rivets, magnets, cable ties, adhesives, hook-and-loop fasteners, or any other similar element(s) as may be apparent to those skilled in the relevant art(s) after reading the description herein.

In some aspects, sensors 1606 may have to be powered on, such as by using a switch. In some additional aspects, sensors 1606 are continuously powered on. In still some additional aspects, sensors 1606 power on automatically when engaged by one or more software applications associated with user computing device 1706.

Once sensor(s) 1606 have been prepared, process 2500 proceeds to step 2506.

At step 2506, application software associated with user computing device 1706 is initialized. This may require user 1602 to enter one or more types of log-in information, such as a password, passcode, fingerprint scan, retina scan, voice recognition verification, and the like. Logging-in, while not necessary, may help the application software correctly identify user 1602 in order to provide the most relevant and accurate information for the ensuing user experience. When user 1602 is not required to log-in, user 1602 may simply open the software application on user computer device 1706. In either case, the software application may be installed within user computing device 1706, it may be retrievable from one or more websites, either as a download or as a live session, or, it may be accessible without requiring a download and without visiting a web site, such as, by way of example and not limitation, in the form of an SaaS.

Once the application software session has been initiated, process 2500 proceeds to step 2508.

At step 2508, user 1602 engages in at least one activity event, such as a basic movement like raising one's arm, a more complex movement like a push-up, or a full activity like playing football. If sensor(s) 1606 are attached to the body of user 1602, then sensor(s) 1606 will be engaged when user 1602 moves the part of the body to which sensor(s) are attached. If sensor(s) 1606 are attached to one or more objects, then sensors 1606 will be engaged when user 1602 moves the object. For example, if user 1602 attaches one or more sensor(s) 1606 to a dumbbell, then those sensor(s) 1606 will be engaged as the dumbbell moves. Process 2500 then proceeds to step 2510.

At step 2510, sensor(s) 1606 capture the activity information triggered by the motion they go through as caused by user 1602. This is accomplished by the gyroscopes, accelerometers, magnetometers, and similar subcomponents within sensor(s) 1606 that respond to and can measure changes in position, orientation, vibration, speed, and the like. Process 2500 then proceeds to step 2512. In some aspects, step 2512 may be skipped; in such aspects, process 2500 proceeds directly to step 2514.

At step 2512, the activity event information captured by sensor(s) 1606 is sent to at least one computational database for storage. This helps the application software perform analysis on the information at a later time, as well as helps user 1602 track progress over time by comparing activity event information captured at different times. It is noted that while beneficial, the storage that occurs at step 2512, in some aspects, may be skipped entirely. Once storage is complete, process 2500 proceeds to step 2514.

At step 2514, application software associated with user computing device 1602 performs at least one analytical function on the activity event information captured by sensor(s) 1606. Such analytical function may serve to convert raw captured objective data into information that is meaningful in evaluating at least one activity element of user 1602, such as neuromuscular efficiency, strength, stability, injury likelihood, and calories burned, as well as similar activity elements as may be apparent to those skilled in the relevant art(s) after reading the description herein. Activity elements may be calculated by measuring and analyzing vibrations, speed, movement fluidity, and other similar aspects of sensor 1606 movement, whether sensor(s) 1606 are attached to the body of user 1602 or to objects utilized by user 1602. In some aspects, subjective information form process 2600 (not shown in FIG. 25) may be used as part of the analysis done by the application software. Once at least one form of analysis has been completed, process 2500 may proceed to step 2516.

At step 2516, raw activity event information and/or the analysis of one or more activity events is presented to user 1602 via at least one display screen associated with user computing device 1706. This information may be presented in any appropriate format as may be apparent to those skilled in the relevant art(s) after reading the description herein, including but not limited to numbers (such as the BaziFit score, assessment score, and/or game scores), graphs, charts, representative colors, representative shapes, and the like. In some aspects, the information is saved for later viewing, either automatically or by the initiation of user 1602. Saved information may be deleted at a later time, either manually or automatically. Once the information has been presented, process 2500 may proceed to step 2518.

At step 2518, the application software session associated with user computing device 1706 is terminated. This may be done by closing out of the software application installed on user computing device 1706, closing out of a website hosting the application software, logging out of the application software session, and/or ending the application SaaS session. Once the application software session has been terminated, process 2500 proceeds to step 2520.

At step 2520 process 2500 is terminated and process 2500 ends.

Figure 26:
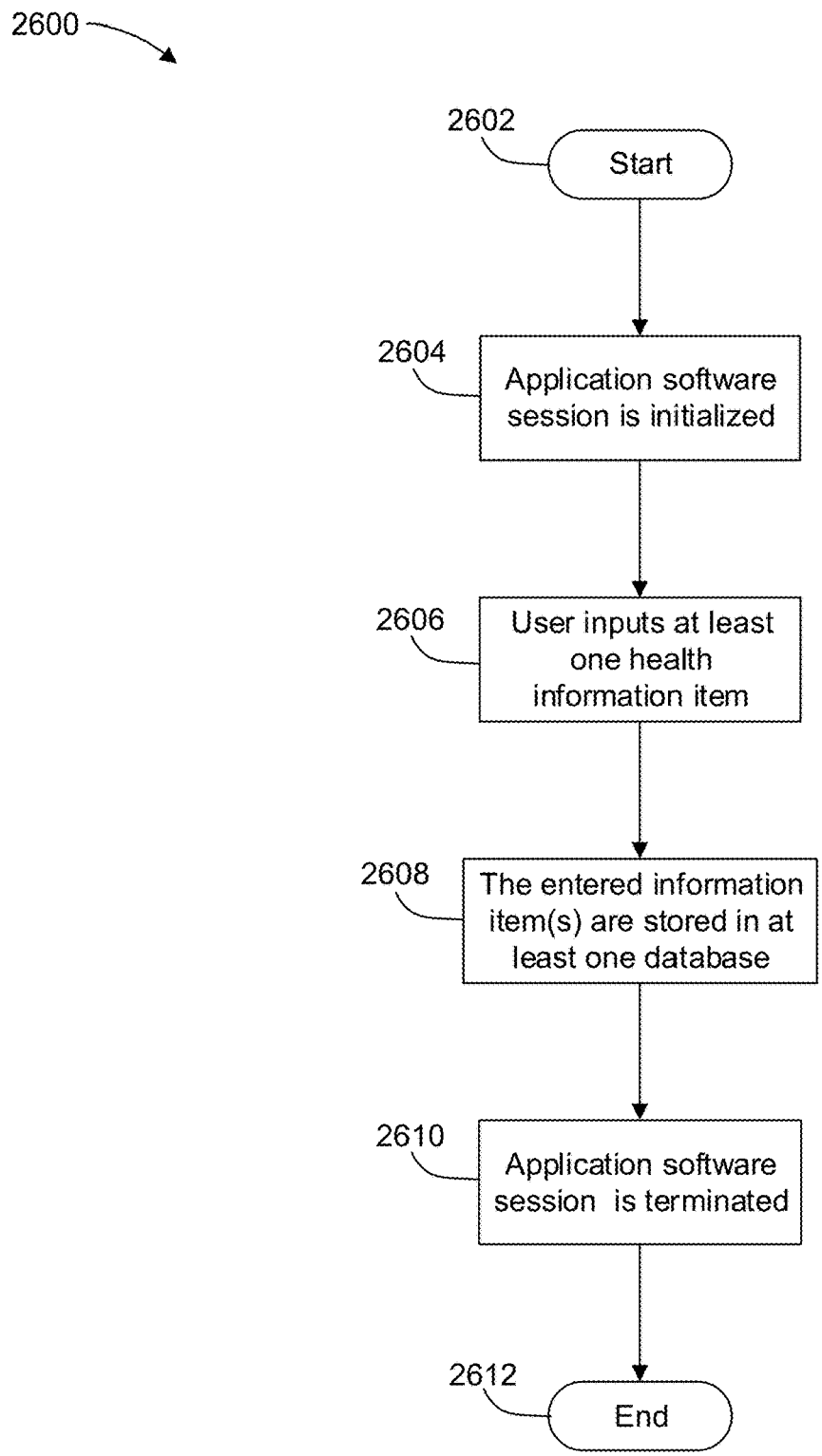
FIG. 26 is a flowchart illustrating an exemplary process for entering at least one input of user health information for use with information gathered by a sensor, according to one aspect of the present disclosure.

Referring now to FIG. 26, a flowchart illustrating an exemplary process 2600 for entering at least one input of user health information for use with information gathered by sensor 1606, according to an aspect of the present disclosure, is shown.

Process 2600 begins at step 2602 with control passing immediately to step 2604.

At step 2604, application software associated with user computing device 1706 is initialized. This may require user 1602 to enter one or more types of log-in information, such as a password, passcode, fingerprint scan, retina scan, voice recognition verification, and the like. Logging-in, while not necessary, may help the application software correctly identify user 1602 in order to provide the most relevant and accurate information for the ensuing user experience. When user 1602 is not required to log-in, user 1602 may simply open the software application on user computer device 1706. In either case, the software application may be installed within user computing device 1706, it may be retrievable from one or more websites, either as a download or as a live session, or, it may be accessible without requiring a download and without visiting a website, such as, by way of example and not limitation, in the form of an SaaS.

Once the application software session has been initiated, process 2600 proceeds to step 2606.

At step 2606, user 1602 inputs at least one health information item into the application software associated with user computing device 1706 using a graphical user interface associated with user computing device 1706. A health information item may include how far user 1602 can run on an injured leg, the range of motion user 1602 has in an uninjured arm compared to an injured arm, how severe pain is during a certain movement, as well as any similar kinds of information as may be apparent to those skilled in the relevant art(s) after reading the description herein. Health information items may be entered using any appropriate techniques, including but not limited to using a keyboard, mouse, joystick, touchscreen, graphical user interface, or any other similar input device as may be apparent to those skilled in the relevant art(s) after reading the description herein. Once at least one health information item has been entered, process 2600 may proceed to step 2608.

At step 2608, the input health information item(s) are sent to at least one computational database for storage. This allows the application software to perform analysis on the information at a later time, as well as helps user 1602 track progress, fitness, health, injury, and/or rehabilitation information by allowing for a comparison between stored input health information item(s) and captured activity event information. Once the desired health information item(s) are stored process 2600 may proceed to step 2610.

At step 2610, the application software session associated with user computing device 1706 is terminated. This may be done by closing out of the software application installed on user computing device 1706, closing out of a website hosting the application software, logging out of the application software, and/or ending the application SaaS session. Once the application software session has been terminated, process 2600 proceeds to step 2612.

At step 2612 process 2600 is terminated and process 2600 ends.

Figure 27:
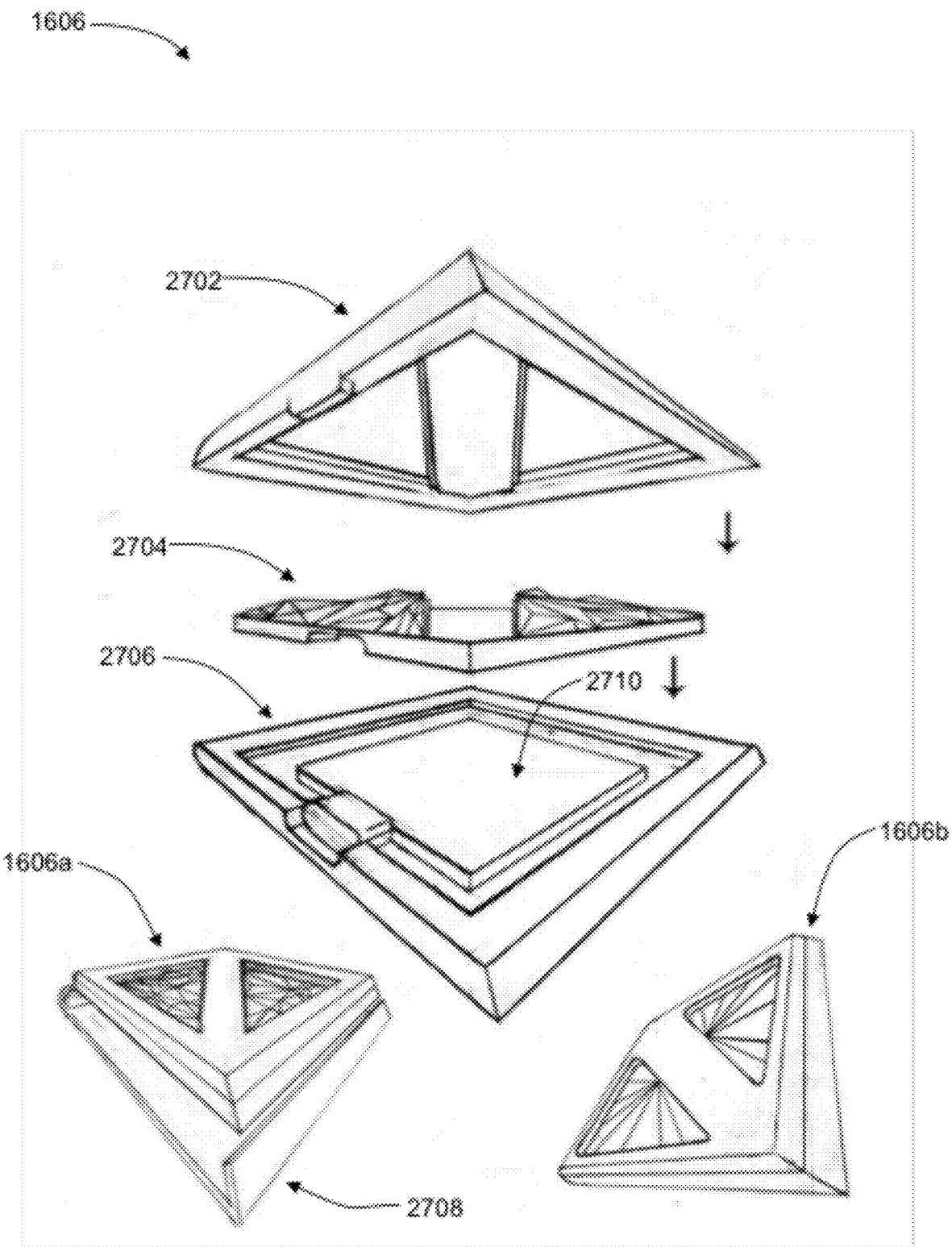
FIG. 27 is an exploded view of an exemplary sensor, according to one aspect of the present disclosure.
Figure 28:
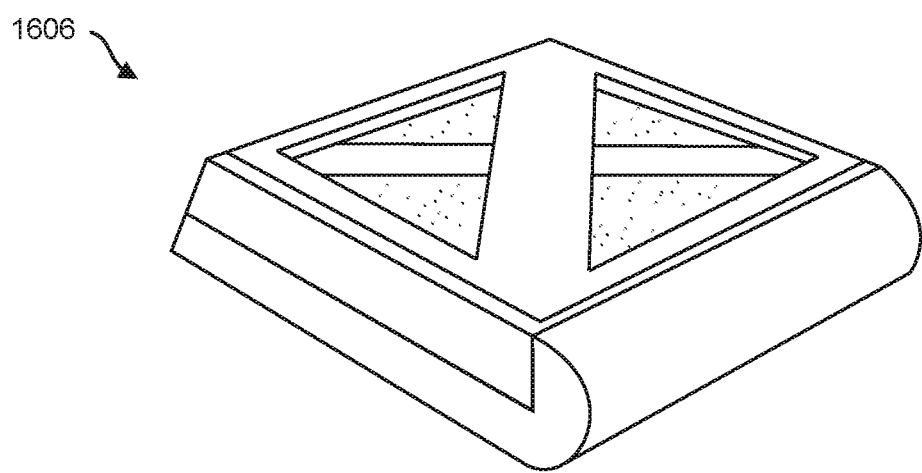
FIG. 28 is a perspective view of a second exemplary sensor, according to one aspect of the present disclosure.
Figure 29:
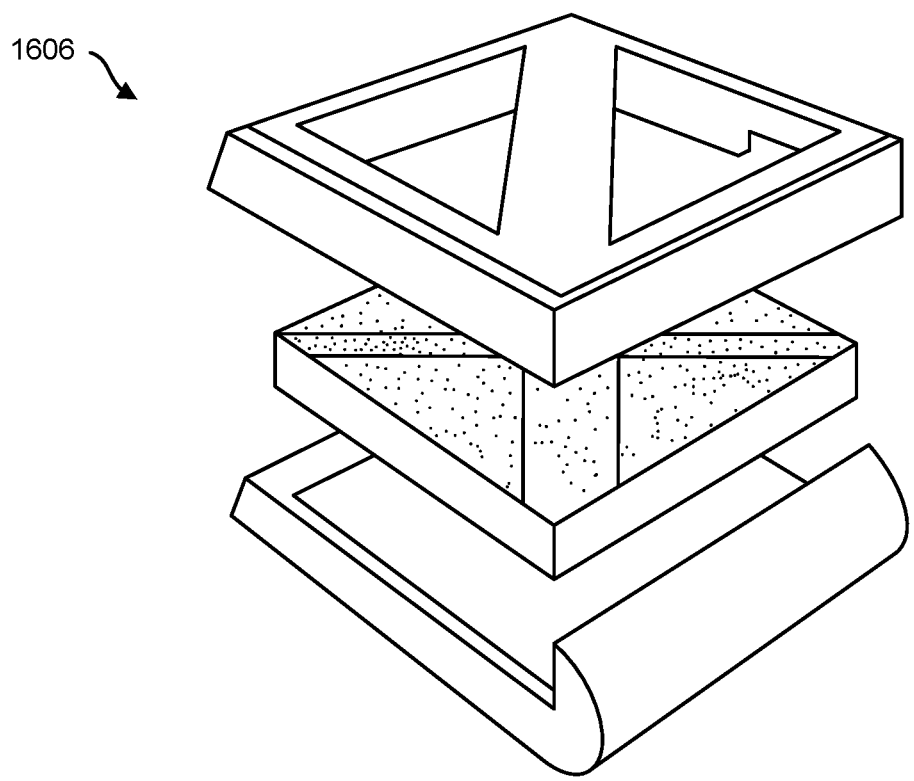
FIG. 29 is an exploded view of a second exemplary sensor, according to one aspect of the present disclosure.

Referring now to FIG. 27, an exploded view of an exemplary sensor 1606, according to an aspect of the present disclosure, is shown.

In some aspects, sensor may comprise a rubber exterior cap 2702, a tessellation housing cap 2704, a base and chip foundation 2706, an attachment connector 2708, and a central processing unit (CPU) 2710. Also shown are two complete sensors 1606 (labeled as sensors 1606a-b in FIG. 27).

Figure 30:
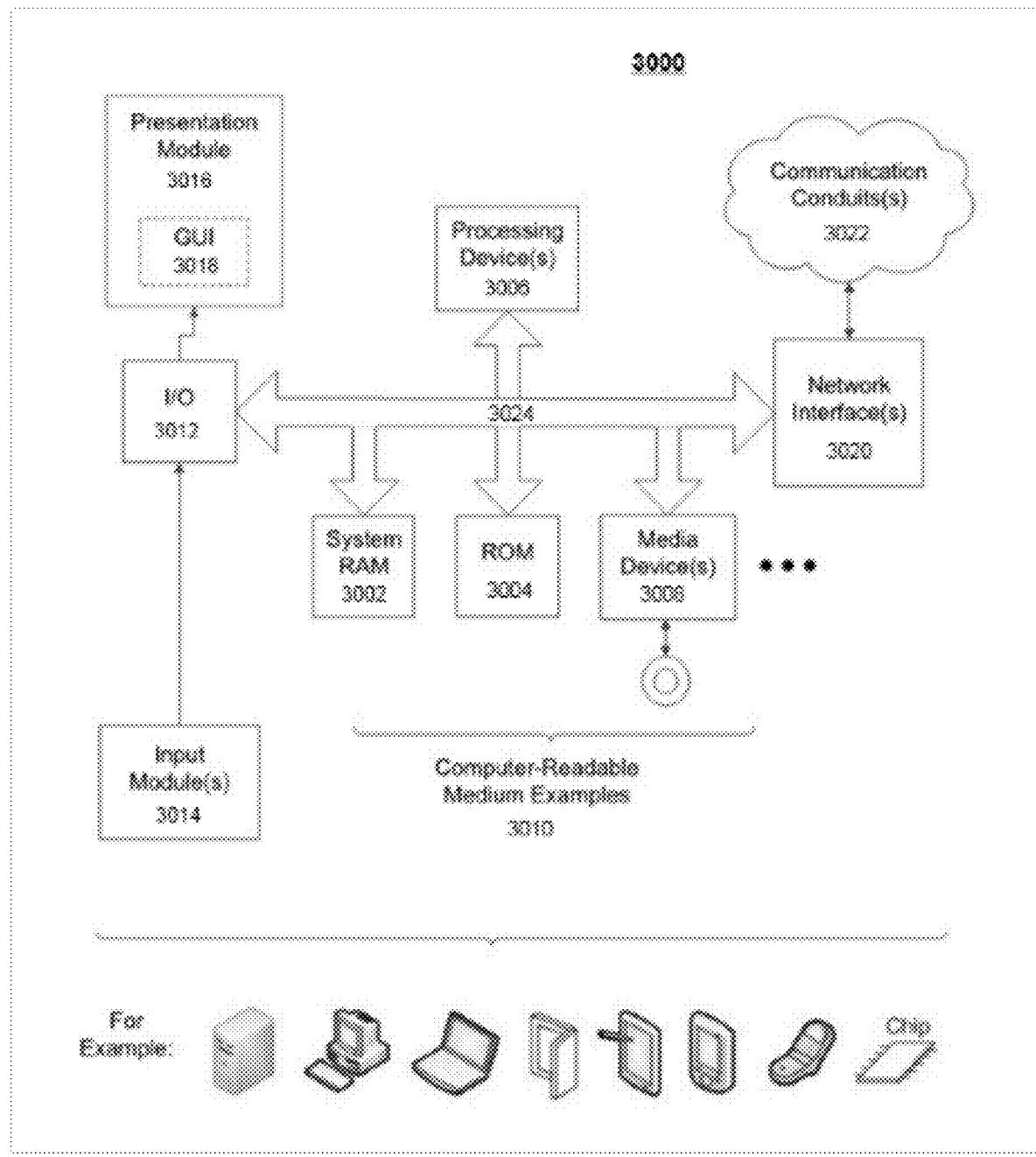
FIG. 30 is a block diagram of an example computing system useful for implementing various embodiments of the present disclosure.

Referring now to FIG. 30, a block diagram of an exemplary computer system useful for implementing various aspects the processes disclosed herein, in accordance with one or more aspects of the present disclosure, is shown.

FIG. 30 sets forth an illustrative computer system that may be used to implement computing functionality 3000, which in all cases represents one or more physical and tangible processing mechanisms.

Computing functionality 3000 may comprise volatile and non-volatile memory, such as RAM 3002 and ROM 3004, as well as one or more processing devices 3006 (e.g., one or more central processing units (CPUs), one or more graphical processing units (GPUs), and the like). Computing functionality 3000 also optionally comprises various media devices 3008, such as a hard disk module, an optical disk module, and so forth. Computing functionality 3000 may perform various operations identified above when the processing device(s) 3006 executes instructions that are maintained by memory (e.g., RAM 3002, ROM 3004, and the like).

More generally, instructions and other information may be stored on any computer readable medium 3010, including, but not limited to, static memory storage devices, magnetic storage devices, and optical storage devices. The term "computer readable medium" also encompasses plural storage devices. In all cases, computer readable medium 3010 represents some form of physical and tangible entity. By way of example, and not limitation, computer readable medium 3010 may comprise "computer storage media" and "communications media."

"Computer storage media" comprises volatile and non-volatile, removable and non-removable media implemented in any method or technology for storage of information, such as computer readable instructions, data structures, program modules or other data. Computer storage media may be, for example, and not limitation, RAM 3002, ROM 3004, EEPROM, Flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

"Communication media" typically comprise computer readable instructions, data structures, program modules, or other data in a modulated data signal, such as carrier wave or other transport mechanism. Communication media may also comprise any information delivery media. The term "modulated data signal" means a signal that has one or more of its characteristics set or changed in such a manner as to encode information in the signal. By way of example, and not limitation, communication media comprises wired media such as a wired network or direct-wired connection, and wireless media such as acoustic, RF, infrared, and other wireless media. Combinations of any of the above are also included within the scope of computer readable medium.

Computing functionality 3000 may also comprise an input/output module 3012 for receiving various inputs (via input modules 3014), and for providing various outputs (via one or more output modules). One particular output mechanism may be a presentation module 3016 and an associated GUI 3018. Computing functionality 3000 may also include one or more network interfaces 3020 for exchanging data with other devices via one or more communication conduits 3022. In some aspects, one or more communication buses 3024 communicatively couple the above-described components together.

Communication conduit(s) 3022 may be implemented in any manner (e.g., by a local area network, a wide area network (e.g., the Internet 120), and the like, or any combination thereof). Communication conduit(s) 3022 may include any combination of hardwired links, wireless links, routers, gateway functionality, name servers, and the like, governed by any protocol or combination of protocols.

Alternatively, or in addition, any of the functions described herein may be performed, at least in part, by one or more hardware logic components. For example, without limitation, illustrative types of hardware logic components that may be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

The terms "service," "module" and "component" as used herein generally represent software, firmware, hardware or combinations thereof. In the case of a software implementation, the service, module or component represents program code that performs specified tasks when executed on one or more processors. The program code may be stored in one or more computer readable memory devices, as described with reference to FIG. 30. The features of the present disclosure described herein are platform-independent, meaning that the techniques can be implemented on a variety of commercial computing platforms having a variety of processors (e.g., desktop, laptop, notebook, tablet computer, personal digital assistant (PDA), mobile telephone, smart telephone, gaming console, and the like).

While various aspects of the present disclosure have been described above, it should be understood that they have been presented by way of example and not limitation. It will be apparent to persons skilled in the relevant art(s) that various changes in form and detail can be made therein without departing from the spirit and scope of the present disclosure. Thus, the present disclosure should not be limited by any of the above described exemplary aspects, but should be defined only in accordance with the following claims and their equivalents.

In addition, it should be understood that the figures in the attachments, which highlight the structure, methodology, functionality and advantages of the present disclosure, are presented for example purposes only. The present disclosure is sufficiently flexible and configurable, such that it may be implemented in ways other than that shown in the accompanying figures (e.g., implementation within computing devices and environments other than those mentioned herein). As will be appreciated by those skilled in the relevant art(s) after reading the description herein, certain features from different aspects of the systems, methods and computer program products of the present disclosure may be combined to form yet new aspects of the present disclosure.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

What is claimed is:

1. A system for facilitating the evaluation of at least one user activity element, comprising:
    at least one computing device operated by at least one user, the at least one computing device being configured to communicate with at least one application server via a communications network;
    at least one sensor configured to communicate via the communications network and detect at least one user activity event record, wherein the at least one sensor is removably attachable to at least one or more of: an object and a user's body;
    at least one computational database; and
    at least one application server configured to communicate, via the communications network, with the at least one computing device, the at least one sensor, and the at least one computational database; wherein the at least one application server comprises:
        a data receiving means configured to receive data from at least one or more of: the at least one sensor and the at least one computing device, and store the received data in the at least one computational database, wherein the received data is retrievable by the at least one user;
        a data analyzing means configured to analyze at least one aspect of the received data, wherein at least one form of the data analyzing means comprises a comparison function; and
        a presentation means configured to provide the received data to the at least one user, including any analysis that has been performed on the data, by presenting the data to the at least one user via the at least one computing device.

2. The system of claim 1, wherein the object comprises at least one activity device.

3. The system of claim 2, wherein the at least one activity device comprises at least one or more of: a barbell, suspension training cables, a balance training device, resistance bands, a surfboard, a balance board, a skateboard, a snowboard, water skis, and snow skis.

4. The system of claim 1, wherein the at least one sensor comprises at least one subcomponent, the at least one subcomponent comprising at least one of: an accelerometer, a gyroscope, a magnetometer, and a computer processor.

5. The system of claim 4, wherein the at least one sensor further comprises at least one output component for communicating with the at least one user, wherein the at least one output component comprises at least one or more of: a visual output component and an audio output component.

6. The system of claim 5, wherein the visual output component comprises at least one light source capable of emitting at least two different wavelengths.

* * * * *